(12) United States Patent
Shohat et al.

(10) Patent No.: US 8,894,713 B2
(45) Date of Patent: Nov. 25, 2014

(54) SHOULDER IMPLANT

(71) Applicant: Ortho-Space Ltd., Caesarea (IL)

(72) Inventors: Shaul Shohat, Kfar HaOranim (IL); Assaf Dekel, Or Yehuda (IL); Ronny Winshtein, Ramat-HaSharon (IL)

(73) Assignee: Ortho-Space Ltd., Kfar-Saba (IL)

( * ) Notice: Subject to any disclaimer, the term of this patent is extended or adjusted under 35 U.S.C. 154(b) by 0 days.

(21) Appl. No.: 14/084,210

(22) Filed: Nov. 19, 2013

(65) Prior Publication Data

US 2014/0074245 A1 Mar. 13, 2014

Related U.S. Application Data

(63) Continuation of application No. 13/811,069, filed as application No. PCT/IL2011/000637 on Aug. 4, 2011, now abandoned.

(60) Provisional application No. 61/370,525, filed on Aug. 4, 2010.

(51) Int. Cl.
*A61F 2/40* (2006.01)
*A61B 17/56* (2006.01)
*A61F 2/30* (2006.01)
*A61B 17/02* (2006.01)
*A61F 2/46* (2006.01)

(52) U.S. Cl.
CPC ............. *A61F 2/4081* (2013.01); *A61B 17/562* (2013.01); *A61F 2002/30581* (2013.01); *A61F 2002/4088* (2013.01); *A61F 2002/30784* (2013.01); *A61F 2002/30586* (2013.01); *A61F 2002/302* (2013.01); *A61F 2002/30909* (2013.01); *A61F 2/30756* (2013.01); *A61F 2002/30576* (2013.01); *A61F 2210/0061* (2013.01); *A61F 2/40* (2013.01); *A61F 2002/30754* (2013.01); *A61B 17/025* (2013.01); *A61F 2002/4635* (2013.01); *A61F 2002/30578* (2013.01); *A61F 2002/30677* (2013.01)
USPC ............................ 623/19.13; 606/90

(58) Field of Classification Search
None
See application file for complete search history.

(56) References Cited

U.S. PATENT DOCUMENTS

| 4,513,058 | A | 4/1985 | Martin |
| 5,176,692 | A | 1/1993 | Wilk et al. |
| 5,282,785 | A | 2/1994 | Shapland et al. |
| 5,286,254 | A | 2/1994 | Shapland et al. |

(Continued)

FOREIGN PATENT DOCUMENTS

| DE | 102007018341 | 10/2008 |
| DE | 102007051782 | 5/2009 |

(Continued)

OTHER PUBLICATIONS

Office Action Dated May 26, 2014 From the State Intellectual Property Office of the People's Republic of China Re. Application No. 200880015430.3 and Its Translation Into English.

(Continued)

*Primary Examiner* — David H Willse
*Assistant Examiner* — Javier Blanco
(74) *Attorney, Agent, or Firm* — Greenberg Traurig, LLP

(57) ABSTRACT

Apparatus and method for a shoulder implant, for example, for the glenohumeral joint. The implant is expandable and deflatable during implantation. The implant is sized for the glenoid fossa. In an exemplary embodiment of the invention, the selection and/or implantation of the implant include adapting the implant by size and function to a particular patient's need.

5 Claims, 14 Drawing Sheets

(56) References Cited

U.S. PATENT DOCUMENTS

| | | | |
|---|---|---|---|
| 5,318,586 | A | 6/1994 | Ereren et al. |
| 5,334,210 | A | 8/1994 | Gianturco et al. |
| 5,336,252 | A | 8/1994 | Cohen |
| 5,458,612 | A | 10/1995 | Chin |
| 5,514,153 | A | 5/1996 | Bonutti |
| 5,516,522 | A | 5/1996 | Peyman et al. |
| 5,547,472 | A | 8/1996 | Onishi et al. |
| 5,641,505 | A | 6/1997 | Bowald et al. |
| 5,653,758 | A | 8/1997 | Daniels et al. |
| 5,720,762 | A | 2/1998 | Bass |
| 5,769,884 | A | 6/1998 | Solovay |
| 5,776,159 | A | 7/1998 | Young |
| 6,019,781 | A | 2/2000 | Worland |
| 6,102,928 | A | 8/2000 | Bonutti |
| 6,187,023 | B1 | 2/2001 | Bonutti |
| 6,214,045 | B1 | 4/2001 | Corbitt et al. |
| 6,248,131 | B1 | 6/2001 | Felt et al. |
| 6,371,904 | B1 | 4/2002 | Sirimanne et al. |
| 6,527,693 | B2 | 3/2003 | Munro, III et al. |
| 6,638,308 | B2 | 10/2003 | Corbitt et al. |
| 6,746,465 | B2 | 6/2004 | Diederich et al. |
| 6,800,082 | B2 | 10/2004 | Rousseau |
| 6,881,226 | B2 | 4/2005 | Corbitt et al. |
| 6,932,834 | B2 | 8/2005 | Lizardi et al. |
| 7,001,431 | B2 | 2/2006 | Bao et al. |
| 7,077,865 | B2 | 7/2006 | Bao et al. |
| 7,144,398 | B2 | 12/2006 | Chern Lin et al. |
| 7,404,791 | B2 | 7/2008 | Linares et al. |
| 7,524,274 | B2 | 4/2009 | Patrick et al. |
| 7,601,113 | B2 | 10/2009 | Lebovic et al. |
| 7,632,291 | B2 | 12/2009 | Stephens et al. |
| 7,637,948 | B2 | 12/2009 | Corbitt |
| 7,713,301 | B2 | 5/2010 | Bao et al. |
| 7,766,965 | B2 | 8/2010 | Bao et al. |
| 7,871,438 | B2 | 1/2011 | Corbitt |
| 2001/0004710 | A1 | 6/2001 | Felt et al. |
| 2001/0041936 | A1 | 11/2001 | Corbitt et al. |
| 2002/0010514 | A1 | 1/2002 | Burg et al. |
| 2002/0016626 | A1 | 2/2002 | DiMatteo et al. |
| 2002/0052653 | A1 | 5/2002 | Durgin |
| 2002/0058947 | A1 | 5/2002 | Hochschuler et al. |
| 2003/0028196 | A1 | 2/2003 | Bonutti |
| 2003/0036728 | A1 | 2/2003 | Samson et al. |
| 2003/0078602 | A1 | 4/2003 | Rousseau |
| 2003/0105469 | A1 | 6/2003 | Karmon |
| 2003/0181939 | A1 | 9/2003 | Bonutti |
| 2003/0195628 | A1 | 10/2003 | Bao et al. |
| 2003/0220649 | A1 | 11/2003 | Bao et al. |
| 2004/0038874 | A1 | 2/2004 | Omoigui |
| 2004/0049269 | A1 | 3/2004 | Corbitt et al. |
| 2004/0073107 | A1 | 4/2004 | Sioshansi et al. |
| 2004/0097794 | A1 | 5/2004 | Bonutti |
| 2004/0133280 | A1 | 7/2004 | Trieu |
| 2004/0143285 | A1 | 7/2004 | Bonutti |
| 2004/0254625 | A1 | 12/2004 | Stephens et al. |
| 2004/0267315 | A1 | 12/2004 | Wolf et al. |
| 2005/0018762 | A1 | 1/2005 | Aiello et al. |
| 2005/0245938 | A1 | 11/2005 | Kochan |
| 2005/0251245 | A1 | 11/2005 | Sieradzki et al. |
| 2005/0273075 | A1 | 12/2005 | Krulevitch et al. |
| 2005/0278025 | A1 | 12/2005 | Ku et al. |
| 2006/0002967 | A1 | 1/2006 | Smestad et al. |
| 2006/0100475 | A1 | 5/2006 | White et al. |
| 2006/0100629 | A1 | 5/2006 | Lee |
| 2006/0106361 | A1 | 5/2006 | Muni et al. |
| 2006/0147492 | A1 | 7/2006 | Hunter et al. |
| 2006/0149380 | A1 | 7/2006 | Lotz et al. |
| 2006/0182780 | A1 | 8/2006 | Riley et al. |
| 2006/0205992 | A1 | 9/2006 | Lubock et al. |
| 2006/0233852 | A1 | 10/2006 | Milbocker |
| 2006/0241766 | A1 | 10/2006 | Felton et al. |
| 2006/0253200 | A1 | 11/2006 | Bao et al. |
| 2007/0038292 | A1 | 2/2007 | Danielpour |
| 2007/0038300 | A1 | 2/2007 | Bao et al. |
| 2007/0078477 | A1 | 4/2007 | Heneveld, Sr. et al. |
| 2007/0118218 | A1 | 5/2007 | Hooper |
| 2007/0198022 | A1 | 8/2007 | Lang et al. |
| 2008/0033471 | A1 | 2/2008 | Paz et al. |
| 2008/0228025 | A1 | 9/2008 | Quick |
| 2008/0269897 | A1 | 10/2008 | Joshi et al. |
| 2009/0048683 | A1 | 2/2009 | Morris et al. |
| 2009/0112214 | A1 | 4/2009 | Philippon et al. |
| 2009/0187252 | A1 | 7/2009 | Howald et al. |
| 2009/0312807 | A1 | 12/2009 | Boudreault et al. |
| 2010/0023127 | A1 | 1/2010 | Shohat |
| 2010/0069947 | A1 | 3/2010 | Sholev et al. |
| 2010/0121445 | A1 | 5/2010 | Corbitt |
| 2010/0191332 | A1 | 7/2010 | Euteneuer et al. |
| 2011/0082547 | A1 | 4/2011 | Corbitt |
| 2011/0295226 | A1 | 12/2011 | Shohat et al. |
| 2012/0179251 | A1 | 7/2012 | Corbitt |
| 2012/0253097 | A1 | 10/2012 | Shohat et al. |
| 2013/0116794 | A1 | 5/2013 | Shohat et al. |
| 2014/0296987 | | 10/2014 | Shohat |

FOREIGN PATENT DOCUMENTS

| | | |
|---|---|---|
| EP | 0507645 | 10/1992 |
| JP | 06-510450 | 11/1994 |
| JP | 10-504202 | 4/1998 |
| JP | 2003-325685 | 11/2003 |
| JP | 2006-247257 | 9/2006 |
| WO | WO 93/04727 | 3/1993 |
| WO | WO 95/33502 | 12/1995 |
| WO | WO 2005/105172 | 11/2005 |
| WO | WO 2006/001009 | 1/2006 |
| WO | WO 2006/055516 | 5/2006 |
| WO | WO 2006/074879 | 7/2006 |
| WO | WO 2007/002561 | 1/2007 |
| WO | WO 2007/054934 | 5/2007 |
| WO | WO 2007/125060 | 11/2007 |
| WO | WO 2008/111073 | 9/2008 |
| WO | WO 2008/111078 | 9/2008 |
| WO | WO 2008/139473 | 11/2008 |
| WO | WO 2008/157727 | 12/2008 |
| WO | WO 2012/017438 | 2/2012 |

OTHER PUBLICATIONS

Search Report Dated May 26, 2014 From the State Intellectual Property Office of the People's Republic of China Re. Application No. 200880015430.3 and its Translation Into English.
Requisition by the Examiner Dated Apr. 30, 2014 From the Canadian Intellectual Property Office Re. Application No. 2,680,812.
Invitation to Pay Additional Fees Dated Sep. 17, 2008 From the International Searching Authority Re. Application No. PCT/IL08/00354.
Applicant-Initiated Interview Summary Dated Feb. 15, 2013 From the US Patent and Trademark Office Re. U.S. Appl. No. 12/531,332.
Communication Pursuant to Article 94(3) EPC Dated Dec. 1, 2011 From the European Patent Office Re. Application No. 05754685.5.
Communication Pursuant to Article 94(3) EPC Dated Feb. 16, 2012 From the European Patent Office Re. Application No. 08738353.5.
Communication Pursuant to Article 94(3) EPC Dated Dec. 21, 2012 From the European Patent Office Re. Application No. 08738353.5.
Communication Pursuant to Rule 70(2) and 70a(2) EPC Dated May 24, 2013 From the European Patent Office Re. Application No. 08719972.5.
Communication Pursuant to Rules 70(2) and 70a(2) EPC Dated Jun. 24, 2011 From the European Patent Office Re. Application No. 08738353.5.
Communication Relating to the Results of the Partial International Search Dated Nov. 3, 2011 From the International Searching Authority Re. Application No. PCT/IL2011/000637.
Communication Relating to the Results of the Partial International Search Dated Nov. 18, 2005 From the International Searching Authority Re.: Application No. PCT/IL2005/000672.
Examiner's Report Dated Apr. 28, 2010 From the Australian Government, IP Australia Re. Application No. 2005257050.
International Preliminary Report on Patentability Dated Feb. 14, 2013 From the International Bureau of WIPO Re. Application No. PCT/IL2011/000637.

(56) References Cited

OTHER PUBLICATIONS

International Preliminary Report on Patentability Dated Jan. 21, 2010 From the International Bureau of WIPO Re.: Application No. PCT/IL2008/000347.
International Preliminary Report on Patentability Dated Jan. 21, 2010 From the International Bureau of WIPO Re.: Application No. PCT/IL2008/000662.
International Preliminary Report on Patentability Dated Oct. 22, 2009 From the International Bureau of WIPO Re.: Application No. PCT/IL2008/000354.
International Preliminary Report on Patentability Dated Jul. 27, 2006 From the International Preliminary Examining Authority Re.: Application No. PCT/IL2005/000672.
International Search Report and the Written Opinion Dated Jan. 9, 2012 From the International Searching Authority Re. Application No. PCT/IL2011/000637.
International Search Report and the Written Opinion Dated Oct. 23, 2008 From the International Searching Authority Re.: Application No. PCT/IL08/00662.
International Search Report Dated Nov. 20, 2008 From the International Searching Authority Re.: Application No. PCT/IL08/00347.
International Search Report Dated Feb. 22, 2006 From the International Searching Authority Re.: Application No. PCT/IL2005/000672.
International Search Report Dated Nov. 26, 2008 From the International Searching Authority Re.: Application No. PCT/IL08/00354.
Invitation to Pay Additional Fees Dated Sep. 23, 2008 From the International Searching Authority Re.: Application No. PCT/IL08/00347.
Notice of Allowance Dated Mar. 8, 2013 From the US Patent and Trademark Office Re. U.S. Appl. No. 15/599,823.
Notice of Allowance Dated Mar. 14, 2012 From the US Patent and Trademark Office Re.: U.S. Appl. No. 11/630,257.
Notification of Publication of Patent Application for Invention and Entering the Substantive Examination Proceeding Dated Oct. 13, 2010 From the Patent Office of the People's Republic of China Re. Application No. 200880015430.3.
Notification of Publication of Patent Application for Invention and Entering the Substantive Examination Proceeding Dated Jul. 28, 2010 From the Patent Office of the People's Rebublic of China Re. Application No. 200880024447.5 and Its Translation Into English.
Office Action Dated Jun. 10, 2013 From the Israel Patent Office Re. Application No. 200939 and Its Translation Into English.
Office Action Dated Nov. 18, 2012 From the Israel Patent Office Re.: Application No. 180270 and Its Translation Into English.
Office Action Dated Nov. 20, 2012 From the Israel Patent Office Re. Application No. 200939 and Its Translation Into English.
Office Action Dated Oct. 27, 2009 From the Israel Patent Office Re.: Application No. 180270 and Its Translation Into English.
Office Action Dated Oct. 30, 2013 From the Israel Patent Office Re. Application No. 200939 and Its Translation Into English.
Official Action Dated Oct. 1, 2012 From the US Patent and Trademark Office Re. U.S. Appl. No. 15/599,823.
Official Action Dated Jun. 8, 2009 From the US Patent and Trademark Office Re.: U.S. Appl. No. 11/630,257.
Official Action Dated Sep. 11, 2013 From the US Patent and Trademark Office Re. U.S. Appl. No. 12/531,332.
Official Action Dated Aug. 13, 2012 From the US Patent and Trademark Office Re. U.S. Appl. No. 12/531,332.
Official Action Dated Apr. 14, 2010 From the US Patent and Trademark Office Re.: U.S. Appl. No. 11/630,257.
Official Action Dated Feb. 14, 2013 From the US Patent and Trademark Office Re. U.S. Appl. No. 12/764,238.
Official Action Dated Apr. 15, 2013 From the US Patent and Trademark Office Re. U.S. Appl. No. 12/531,073.
Official Action Dated Aug. 19, 2009 From the US Patent and Trademark Office Re.: U.S. Appl. No. 11/630,257.
Official Action Dated Jul. 19, 2013 From the US Patent and Trademark Office Re. U.S. Appl. No. 13/811,069.
Official Action Dated Feb. 22, 2013 From the US Patent and Trademark Office Re. U.S. Appl. No. 12/531,332.
Official Action Dated Oct. 31, 2012 From the US Patent and Trademark Office Re. U.S. Appl. No. 12/531,073.
Patent Examination Report Dated Jul. 13, 2012 From the Australian Government, IP Australia Re. Application No. 2008224435.
Patent Examination Report Dated Aug. 29, 2013 From the Australian Government, IP Australia Re. Application No. 2008224435.
Patentability Search on Expandable Prostheses Particularly Useful for Rotator Cuff Protection Dated Oct. 31, 2007 Effectuated by Sol Scheinbein.
Request for Reconsideration Filed With an RCE Dated Aug. 9, 2010 to Official Action of Apr. 14, 2010 From the US Patent and Trademark Office Re.: U.S. Appl. No. 11/630,257.
Restriction Official Action Dated Feb. 6, 2012 From the US Patent and Trademark Office Re. U.S. Appl. No. 12/531,073.
Restriction Official Action Dated Dec. 12, 2011 From the US Patent and Trademark Office Re. U.S. Appl. No. 12/531,073.
Restriction Official Action Dated May 23, 2013 From the US Patent and Trademark Office Re. U.S. Appl. No. 13/811,069.
Restriction Official Action Dated Sep. 24, 2012 From the US Patent and Trademark Office Re. U.S. Appl. No. 12/764,238.
Supplementary European Search Report and the European Search Opinion Dated Jun. 6, 2011 From the European Patent Office Re. Application No. 08738353.5.
Supplementary European Search Report and the European Search Opinion Dated May 6, 2013 From the European Patent Office Re. Application No. 08719972.5.
Third Party Submission Under 37 CFR § 1.99 Dated Mar. 26, 2010 in the US Patent and Trademark Office Re. U.S. Appl. No. 12/531,332.
Translation of Decision on Rejection Dated Oct. 16, 2009 From the State Intellectual Property Office of the People's Republic of China Re.: Application No. 200580028684.5.
Translation of Notice of Payment of the Restoration Fee for Unity of Invention Dated Jul. 26, 2011 From the State Intellectual Property Office of the People's Republic of China Re. Application No. 200880014369.0.
Translation of Notice of Reason for Rejection Dated Nov. 5, 2010 From the Japanese Patent Office Re. Application No. 2007-517651.
Translation of Notice of Reason for Rejection Dated Nov. 27, 2012 From the Japanese Patent Office Re. Application No. 2009-553278.
Translation of Office Action Dated Jul. 3, 2009 From the State Intellectual Property Office of the People's Republic of China Re.: Application No. 200580028684.5.
Translation of Office Action Dated Dec. 11, 2012 From the State Intellectual Property Office of the People's Republic of China Re. Application No. 200880015430.3.
Translation of Office Action Dated Jan. 11, 2011 From the State Intellectual Property Office of the People's Republic of China Re. Application No. 200580028684.5.
Translation of Office Action Dated Jul. 11, 2013 From the State Intellectual Property Office of the People's Republic of China Re. Application No. 200880015430.3.
Translation of Office Action Dated Feb. 17, 2012 From the State Intellectual Property Office of the People's Republic of China Re. Application No. 200880015430.3.
Translation of Office Action Dated Oct. 19, 2011 From the State Intellectual Property Office of the People's Republic of China Re. Application No. 200880014369.0.
Translation of Office Action Dated Mar. 28, 2012 From the State Intellectual Property Office of the People's Republic of China Re. Application No. 200880014369.0.
Translation of Office Action Dated Mar. 30, 2012 From the State Intellectual Property Office of the People's Republic of China Re. Application No. 200880024447.5.
Translation of Office Action Dated Oct. 31, 2008 From the State Intellectual Property Office of the People's Republic of China Re.: Application No. 200580028684.5.
Translation of Official Decision of Rejection Dated Jun. 7, 2011 From the Japanese Patent Office Re. Application No. 2007-517651.
Translation of Search Report Dated Jul. 11, 2013 From the State Intellectual Property Office of the People's Republic of China Re. Application No. 200880015430.3.

(56) References Cited

OTHER PUBLICATIONS

Written Opinion Dated Nov. 20, 2008 From the International Searching Authority Re.: Application No. PCT/IL08/00347.
Written Opinion Dated Feb. 22, 2006 From the International Searching Authority Re.: Application No. PCT/IL2005/000672.
Written Opinion Dated Nov. 26, 2008 From the International Searching Authority Re.: Application No. PCT/IL08/00354.
Anderson "Biological Responses to Materials", Annual Review of Materials Research, 31: 81-110, 2001.
Notice of Reason for Rejection Dated Mar. 14, 2014 From the Japanese Patent Office Re. Application No. 2013-99793 and Its Translation Into English.
Office Action Dated Feb. 26, 2014 From the Israel Patent Office Re. Application No. 200939 and Its Translation Into English.
Office Action Dated Jan. 28, 2014 From the State Intellectual Property Office of the People's Republic of China Re. Application No. 200880015430.3.

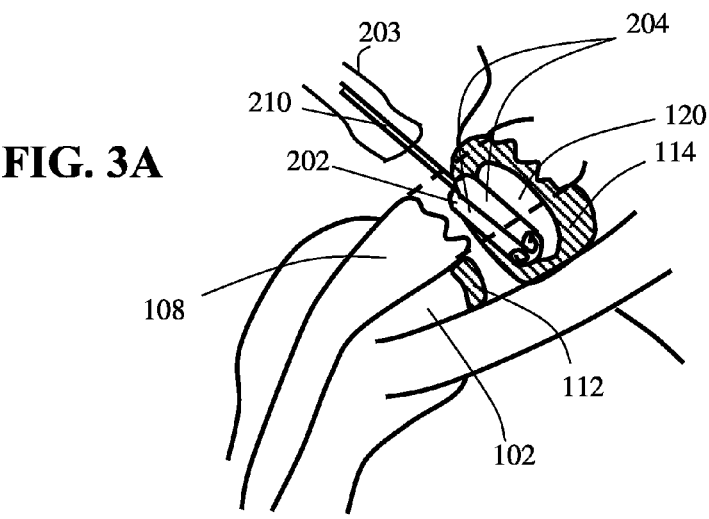
FIG. 3A
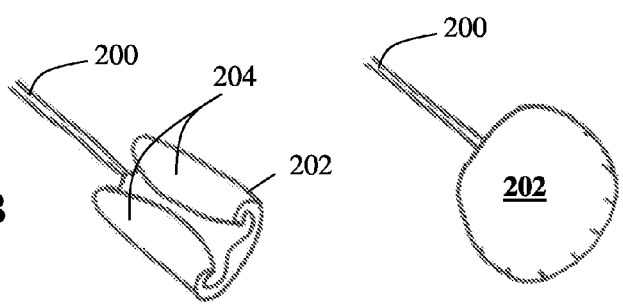
FIG. 3B
FIG. 3C

FIG. 8A
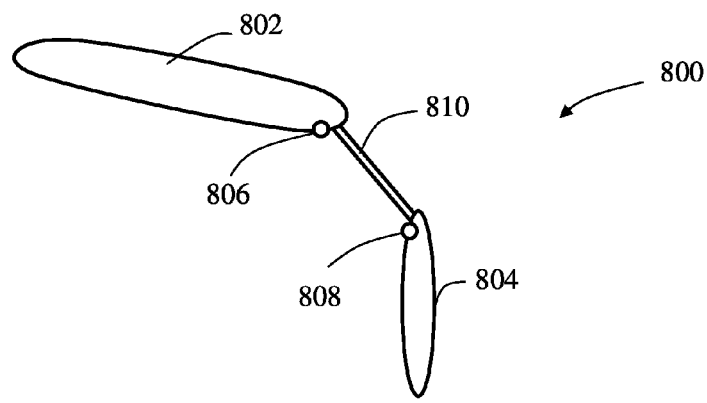
FIG. 8B
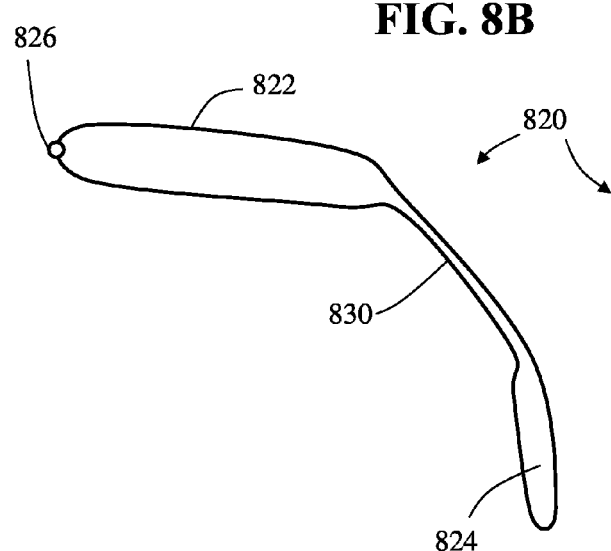
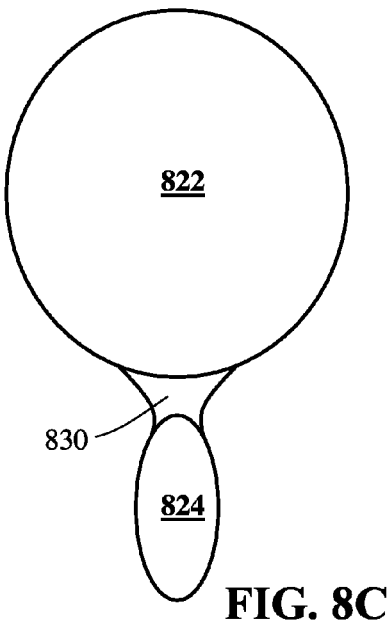
FIG. 8C

SHOULDER IMPLANT

RELATED APPLICATION/S

This application is a continuation of U.S. patent application Ser. No. 13/811,069, filed on Jan. 18, 2013, now abandoned, which is a national phase filing under 35 USC 371 of International Application No. PCT/IL2011/000637, filed on Aug. 4, 2011, and claims the benefit of priority under 35 USC 119(e) of a U.S. provisional application Ser. No. 61/370,525, filed Aug. 4, 2010 and having the title "SHOULDER IMPLANT".

The contents of the above document are incorporated by reference as if fully set forth herein.

FIELD OF THE INVENTION

The present invention generally relates to orthopaedic implants and related methods of treatment, for example, to methods and devices for preventing or treating glenohumeral joints disorders.

BACKGROUND OF THE INVENTION

The shoulder is a very unique joint in the human body having the greatest range of motion while being least stable than other large articular joints. FIGS. 1A-B show different aspects of a human shoulder joint anatomy. There are four separate joints that make up the shoulder; the main one is the glenohumeral joint formed by the humerus head or "ball" 102 and a socket on the scapula denoted as the glenoid 104. The glenoid itself defines a glenoid fossa 120 which is very shallow and small (covering at most only a third of the humerus ball), also relative to other joints in the body, and fitting is accomplished by the presence of the glenoidal labrum 114, a fibrocartilaginous rim attached around the margins of the glenoid fossa/cavity 120 which substantially deepens the glenoid cavity and protects the edges of the bone. The labrum is triangular-like in cross section with its base fixed to the circumference of the cavity. Articular cartilage 110 covers the end extension of the humerus ball (as well as, 112, in the glenoid cavity), a thin layer of a slippery material having a stiff rubbery consistency, mainly serving as a shock absorber (or cushion) and provides an exceptionally smooth surface for an easy relative motion between the ball and socket members. In one aspect the glenohumeral joint differs from the hip joint (the second ball-and-socket type joint in the human body) by the fact that the articular cartilage is substantially thinner and the shocks and impulses and forces applied to it have different amplitudes and different temporal profiles. The glenohumeral joint is maintained in-place by a joint capsule 118 formed by a group of enveloping ligaments. The synovial membrane 116, or synovium, is the inner layer or lining of the joint capsule. It is composed of connective tissue, and secretes a lubricating fluid named synovial, a viscous non-Newtonian fluid which reduces friction to facilitate motion between the joint members in a synovial cavity 106.

The unique combination and correlating configuration of the glenohumeral joint members, namely the capsule, the cartilage and the synovium, allows these incomparable characteristics of the shoulder with respect to other articular joints in the human body. Any disorder of at least one of the joint members may cause dysfunction and at least severe discomfort and pain sensation to the patient. A common disorder is the glenohumeral joint osteoarthritis, or degenerative joint disease, where the cartilage gradually thinned and eventually completely worn out. Besides osteoarthritis, which is the most common type of arthritis, there are also other related illnesses such as rheumatoid arthritis. Synovium can also become irritated and thickened in conditions such as rheumatoid arthritis. Adhesive capsulitis, also known as "frozen shoulder", is a disorder in which the shoulder capsule becomes inflamed and stiff, greatly restricting motion and causing chronic pain. Frozen shoulder may be caused by trauma or injury, and probably involves an autoimmune component and/or indicated in lack of synovial fluid.

The more severe cases of glenohumeral joint disorders are usually treated with surgical intervention known as shoulder arthroplasty, in which the glenohumeral joint or only the humerus head is partially or completely removed and replaced with prosthesis. Arthroscopic introduction of healing regenerative substances and matrixes (such as the Graftjacket®, an acellular dermal matrix allograft manufactured by Wright Medical Group, Inc.) was also tested and found efficient in some cases.

The following examples describe several initiatives to treat general articular joints disorders, though not specifically specified or adapted for the shoulder glenohumeral joint.

European patent publication number 0507645 to Bouvet, the disclosure of which is fully incorporated herein by reference, describes an implant comprising a leak tight envelope made of a flexible, non-elastic material and a fluid incompressibly filling up the envelope, the envelope is capable of being interposed between the two parts of a joint which are to move with respect to each other, and it is in contact with both these parts. According to this document, the implant is intended for reducing production of particles due to wear of joint prostheses after full or partial arthroplasty. Its incompressible character is especially intended for maintaining the two parts of the joint (for example, the "ball" and "socket" members) at a constant distance while allowing natural joint movements without friction of the surfaces in contact. The proposed exemplary embodiment was focused on the coxofemoral or "hip" joint, which, it should be noted, is mechanically, anatomically, medically and functionally different from the shoulder joint.

U.S. patent application Ser. No. 10/865,238 to Ku et al., the disclosure of which is fully incorporated herein by reference, describes a prosthesis for placement into a joint space between two or more bones. The prosthesis includes a body formed from a pre-formed solid one piece elastomer, wherein the elastomer is formed from a synthetic organic polymer that is biocompatible and has a modulus of elasticity and a mechanical strength between 0.5 MPa and 75 MPa. The body having a shape contoured to fit within a joint space between the femoral condyle, tubercle, and tibial plateau without any means of attachment.

U.S. patent application Ser. No. 12/259,907 to Philippon et al., the disclosure of which is fully incorporated herein by reference, describes a device for accessing and distending a joint comprises a distraction structure having a generally tapered distal portion adapted to penetrate a tissue region and create an access space within a joint. The distraction structure also includes a lumen extending from a proximal surface to a distal portion. The device further includes a distention structure deployable through the lumen and adapted to exert a force between a first joint surface and a second joint surface and create a working space. The distention structure may, in some embodiments, include an elongate member having a proximal end, a distal end, and a lumen extending along at least a portion of the length of the elongate member, a first expandable region deployable from a first substantially collapsed position to a second substantially expanded position, the first expandable region adapted to exert a force between the first joint surface from the second joint surface.

US patent publication 2009/0187252 describes an implant for relieving damaged areas of the surfaces of hip or shoulder joints from stress. The implant is cup-shaped or cap-shaped, rests in the socket by means of a convex external face and sits in the condyle by means of a convex external face in the implanted state. The implant comprises at least two articulation layers which are movable relative to each other and encompass articulation surfaces that face one another in the implanted state. Also described is an implantation method where the implant is pushed, using fluid through a channel that is drilled in the trochanter and femoral head, in to a joint space of a hip joint.

SUMMARY OF THE INVENTION

In a broad aspect of some embodiments there is provided a biodegradable inflatable glenohumeral joint prosthesis, optionally adapted to prevent or treat osteoarthritis.

There is provided in accordance with some exemplary embodiments of the invention a method for implanting and deploying an implant in a glenohumeral joint to achieve a desired function, comprising minimally invasively inserting an expandable implant into a joint capsule of said glenohumeral joint and then controlling the expansion of said implant to a desired amount such that said desired function is achieved.

Optionally, said desired function comprises one or more of implant stability, shoulder stability, pain reduction and amelioration of osteoarthritis. Optionally or alternatively, said desired function is a normal unhindered multiaxial motion of a human shoulder under loads of up to 100 Kg that is stabilized only by soft tissues.

In an exemplary embodiment of the invention, controlling the expansion comprises first expanding to assist deployment of the implant and then contracting to said desired amount.

In an exemplary embodiment of the invention, inserting comprises inserting an implant that fits within a glenoid fossa and is maintained in place, at least in part by a Labrum of said glenohumeral joint.

In an exemplary embodiment of the invention, the method comprises anchoring said implant to cartilage of said joint. Optionally, said anchoring comprises anchoring to a single point at the glenoid apex or to at least 3 points on a glenoid cartilage.

In an exemplary embodiment of the invention, the method comprises determining a correctness of said inserting and said controlling by manipulating said joint to ensure a separation between bone faces in said joint, over a range of useful motion thereof.

In an exemplary embodiment of the invention, said implanting is in response to an illness of the joint and wherein said illness is osteoarthritis.

In an exemplary embodiment of the invention, said expandable implant is inflatable and provided detachably connected to inflation means, and wherein said inflation means are detached from said expandable corrective and withdrawn after said controlling.

In an exemplary embodiment of the invention, said controlling comprises controlling said expansion until reaching a maximally allowed parameter including at least one of a pressure, a volume, a diameter and a consistency.

In an exemplary embodiment of the invention, the method comprises:
creating a passage into said glenohumeral joint capsule for said implanting; and
increasing a gap between a humerus head and a glenoid fossa of said glenohumeral joint, before said implanting.

In an exemplary embodiment of the invention, the method comprises:
creating a second passage, to a sub-acromial space; and
inserting a second portion of said collapsed expandable implant into said space.

In an exemplary embodiment of the invention, the method comprises:
forming a channel in the humeral head; and
delivering said implant through said channel. Optionally, the method comprises anchoring said implant to said channel. Optionally or alternatively, the method comprises covering at least 40% of a surface of a bone-bone contact surface said humeral head by said implant.

There is provided in accordance with some exemplary embodiments of the invention an expandable implantable device sized and shaped to include at least a section which fits in a synovial joint capsule such that it sits in a fossa, when in an expanded, deployed form, between and selectively formable from a minimally invasive delivery form to a chosen expanded form smaller in at least one dimension than said deployed expanded form.

Optionally, said device is sized to fit within a glenoid fossa. Optionally or alternatively, said device has a body which fits within a glenoid fossa and one or more anchoring elements which extend onto a Labrum.

In an exemplary embodiment of the invention, said device has a main body shaped to sit in a glenoid fossa and one or more elements which extend out of said fossa, and are thinner over a Labrum than at said main body.

In an exemplary embodiment of the invention, said one or more anchoring element comprises a lip. Optionally or alternatively, said one or more anchoring element comprises a plurality of ears adapted to have anchors attached thereto.

In an exemplary embodiment of the invention, said device is ellipse-like to match a glenoid fossa shape. Optionally or alternatively, said device is circular with a diameter to match an inner diameter of a glenoid fossa.

In an exemplary embodiment of the invention, said device has at least one aperture therethrough.

In an exemplary embodiment of the invention, said device is non-planar to comply, at least in part, with a curvature of said glenoid fossa. Optionally, said device has two faces, each adapted to conform to a bone face and wherein the two faces have different spatial curvatures.

In an exemplary embodiment of the invention, said device is constructed to endure compressive forces of at least 100 Kg over a period of at least 3 years without mechanical failure.

In an exemplary embodiment of the invention, said device can be inflated and deflated during implantation to have a chosen consistency. Optionally, said chosen consistency resembles at least one of a natural healthy bone consistency, a natural healthy articular cartilage consistency, and a natural healthy synovium consistency.

In an exemplary embodiment of the invention, said device is formed of a biodegradable material.

In an exemplary embodiment of the invention, the device comprises at least one connection between two sides of the device other than at its edge, the connection defining a maximum expansion volume of said device. Optionally or alternatively, the device comprises a mesh or other surface adapted to adhere or cause adherence to a joint face.

In an exemplary embodiment of the invention, said device comprises a smooth surface adapted to allow a humeral head to slide on. Optionally or alternatively, said device comprises a smooth surface adapted to allow a glenoid to slide on.

In an exemplary embodiment of the invention, the device comprises an anti-adhesive layer adapted to prevent bone adhesion.

In an exemplary embodiment of the invention, the device comprises at least one anchor adapted for attaching said device to a joint portion. Optionally, said at least one anchor comprises an anchor adapted for attaching said device to a labrum section.

In an exemplary embodiment of the invention, the device comprises a sleeve for surrounding said implant during implantation and a deployment tube incorporating at least one of a seal and a valve for passage of fluid into said device during implantation thereof.

In an exemplary embodiment of the invention, the device comprises a second section, connected to said device by a bridge, which second section is adapted to provide a bursa function to a shoulder joint. Optionally, said bridge comprises a valve.

There is provided in accordance with some exemplary embodiments of the invention an implantable shoulder corrective comprising:

(a) an expandable chamber, enclosing a reservoir, sized and configured to fit in a glenohumeral joint capsule in an expanded form and provide slidability therein;

(b) an extension, sized and shaped to protrude out of said glenohumeral joint capsule when said expandable chamber is in said expanded form, comprising:

a body with at least one smooth surface allowing unhindered movement of a first tissue relative to other tissues;

(c) a bridge connecting said chamber and said extension. Optionally, said bridge and said extension are sized and shaped to provide a bursa function by said extension. Optionally or alternatively, said extension is inflatable. Optionally or alternatively, said extension is in fluid communication with said reservoir. Optionally or alternatively, said extension includes a second smooth surface opposing said first smooth surface.

In an exemplary embodiment of the invention, said expandable chamber defines a peripheral diameter substantially unchangeable by chamber expansion, once deployed, and a height changeable by said chamber expansion.

In an exemplary embodiment of the invention, said chamber comprises a substantially seamless outer surface except for a port and said bridge.

The present invention, in some embodiments thereof, further provides a method for preventing or treating glenohumeral joint osteoarthritis, including:

(a) providing a collapsed inflatable prosthesis releasably attached to an inflation device into a glenohumeral joint capsule;

(b) inflating the inflatable prosthesis via the inflation device until a chosen consistency is met; and (c) detaching the inflation device from the inflatable prosthesis.

In a broad aspect of some embodiments there is provided an expandable implantable device sized to fit inside a synovial joint capsule and selectively formable from a minimally invasive delivery form to an expanded form indicatable by a chosen consistency of the device, wherein the device includes a first smooth surface on which a first cartilage portion may slide. In some embodiments, the synovial joint is a glenohumeral joint. In some embodiments, the chosen consistency resembles a natural healthy bone consistency, a natural healthy articular cartilage consistency, or a natural healthy synovium consistency.

In some embodiments, the device includes an inflatable cavity. Optionally, the cavity is selectively inflatable with a fluid material to the chosen consistency of the device. In some embodiments, the fluid material includes saline, biocompatible gel, synovial fluid, glucosamine, chondroitin, anti-inflammatory agent, or any combination thereof.

In some embodiments, the device includes a biodegradable material. Optionally, the biodegradable material includes PLA, PLGA, caprolactone, polycaprolactone, polydiaxone, or any combination thereof. In some embodiments, the device is designed to rupture within a time period of 1 to 30 weeks, optionally 6 to 10 or 12 weeks, following expansion. Optionally, the device is designed to completely biodegrade within a time period of 3-30 months, optionally 6-12 months, following expansion.

In some embodiments, the device includes at least one passage extending from a first side to a second side of the device for promoting fibrotic development therein. Optionally, at least one passage defines a maximum expansion volume of the device.

In some embodiments, the device includes a mesh.

In some embodiments, the device is configured to cushion between a ball-like bone portion and a socket-like bone portion. Optionally, the first smooth surface is located on a proximal side of the device. Optionally, the first cartilage portion is associated to a humerus. In some embodiments, the device includes a distal side with a second smoothed surface on which a second cartilage portion may slide. Optionally, the second cartilage portion is associated to a glenoid. Alternatively or additionally, the device includes an anti-adhesive applied to the smooth surface on the proximal side and/or on the distal side to prevent bone adhesion.

In some embodiments, the device includes an anchor, or plurality of anchors, adapted for attaching the device to an articular capsule. Optionally, the anchor adapted for attaching the device to a bone and/or to a labrum.

In some embodiments, the device includes a sleeve incorporating at least one of a seal and a valve.

In some embodiments, the device expansion is irreversible.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-C illustrate different deployment stages of a prosthesis, in accordance with an exemplary embodiment of the invention;

FIGS. 8A-8C are side, side and top views of two-section prostheses, in accordance with exemplary embodiments of the invention;

DETAILED DESCRIPTIONS OF EXEMPLARY EMBODIMENTS

Figure 1A:
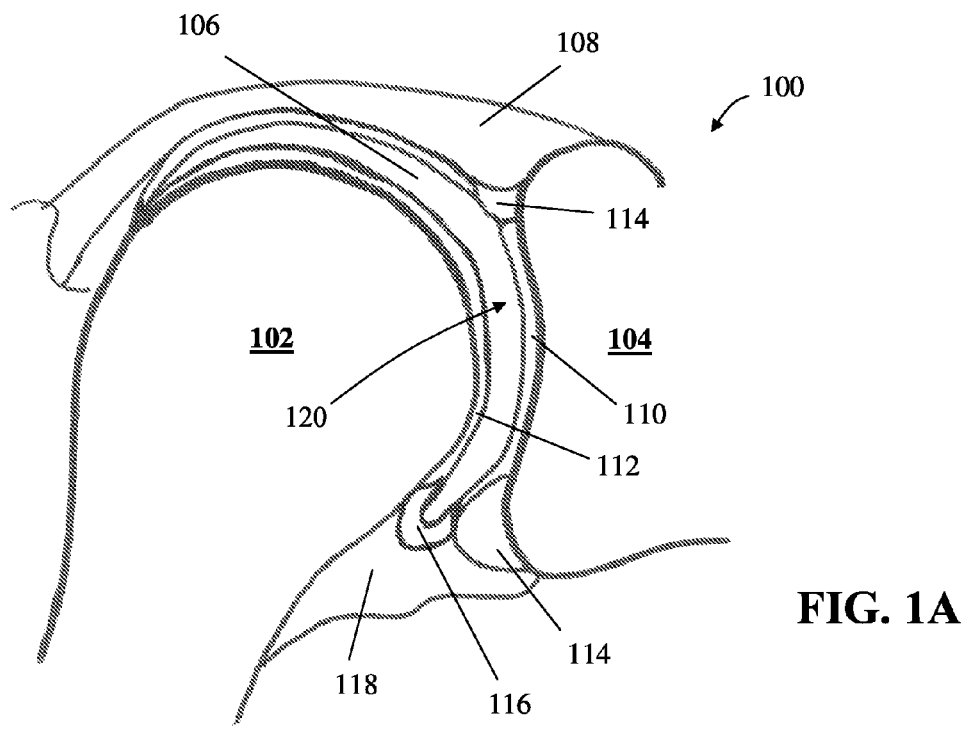
FIGS. 1A-B illustrate different anatomical views of a glenohumeral joint.
Figure 1B:
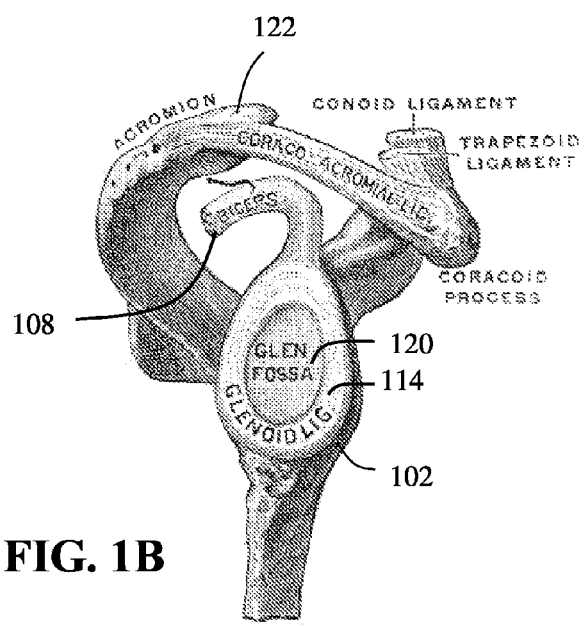

The present invention generally relates to orthopaedic implants and related methods of treatment, for example, to methods and devices for preventing or treating glenohumeral joints disorders.

An aspect of some embodiments of the invention relates to a method of providing an implant in the shoulder, between two bones, in which the implant is implanted and then inflated such that it is suitable for use in the shoulder joint, for example, the glenohumeral joint portion thereof.

In an exemplary embodiment of the invention, the implant is sized and shaped to fit in the glenoid fossa and is optionally held in place also or only by the surrounding Labrum. In an exemplary embodiment of the invention, the implant covers at least 30%, 50%, 70%, 90% or intermediate or greater percentages of the surface area of the Glenoid Fossa. Optionally, the implant is selected to match the shape of the fossa (e.g., be oval or elliptical in shape with an optional sharper edge) and/or its diameter. Optionally or alternatively, the implant is selected so it cannot rotate and/or move transversally within the fossa. Optionally or alternatively, the implant includes one or more recesses and/or opening therein, for example, being donut shaped. In some embodiments, the entire implant (e.g., excepting anchoring) fits within the fossa. In others, the implant includes a section or body shaped to sit in the fossa but has anatomically functional sections (e.g., other than anchoring or inflation) which extend onto or past the labrum.

In an exemplary embodiment of the invention, one or more anchoring elements are used. Optionally at least one anchor is adapted for fixating the implant to a labrum portion. Optionally or alternatively, at least one of the implant faces or surfaces is curved, to match a shape of the Humerus and/or of a Glenoid. Optionally, the implant has different curvatures on two opposing surfaces thereof.

In an exemplary embodiment of the invention, the implant is provided at a location and/or anchored in a manner which matches rotation positions where friction and/or pain are expected. Optionally, the thickness of the implant is non-uniform at one or more edges thereof, for example, tapering, where movement of the joint may allow bone to slide past other bone without an intermediate implant section.

In an exemplary embodiment of the invention, the selection and implantation process include a personalization to the patient. Optionally, the implementation includes a fine-tuning process where fit of, for example, implant inflation, is matched to dynamic properties of the patients joint. In an exemplary embodiment of the invention, the inflation matching includes first over inflating to deploy the implant and then reducing inflation amount to a functionally desired inflation of the implant. Optionally, alternatively or additionally, the selection process includes matching of the implant to the patient anatomy, for example, to the Glenoid Fossa and/or humeral head.

In an exemplary embodiment of the invention, the implant is made strong enough to withstand the high forces in the shoulder, for example, its wall is made thick enough to resist forces of at least 100-200 Kg. Alternatively or additionally, the implant wall is made thick enough to resist a pressure across its wall of at least 2-3 atm. Optionally, the implant has a wall thickness of between 0.1 and 0.5 mm, for example, about 0.25 mm In an exemplary embodiment of the invention, the implant includes one or more extensions. For example, the implant may include an extension to lie between a tendon and the bone and/or to occupy a volume in a subacromial space.

In an exemplary embodiment of the invention, the implant is configured to cover a humeral head, optionally anchoring to the humeral head.

In an exemplary embodiment of the invention, the implant is selected and/or manipulated to match a particular patient. In one example, during implantation, the implant is overinflated to ensure its deployment and then deflated to a working state.

In an exemplary embodiment of the invention, the shoulder is distracted during implantation, optionally by manual manipulation and/or by the over-inflation, and then the distraction removed, for example, to test the implant and/or determine a desired inflation amount.

In an exemplary embodiment of the invention, the shoulder joint is manipulated to determine that the implant is in a correct place and/or does not move.

In an exemplary embodiment of the invention, implanting (and/or optionally manipulation or other acts of tuning) includes making sure that there is no contact between the Humerus and the Glenoid over a desired range of motion.

An aspect of some embodiments of the invention relates to a method of implantation of an implant in a shoulder joint, in which a channel is formed in the bone and the implant is inserted through the channel. In an exemplary embodiment of the invention, the channel is a hole drilled through the Humerus head. Optionally, the implant is inflated and/or deflated through the channel. Optionally or alternatively, the implant includes at least one protrusion which anchors in the channel after deployment of the implant.

In an exemplary embodiment of the invention, the implant is used to cover at least 30%, 50%, 80% or intermediate percentages of the area of the cartilage covered portion of a humeral head. In an exemplary embodiment of the invention, the implant is provided at a location and/or anchored in a manner which matches rotation positions where friction and/or pain are expected. Optionally, the thickness of the implant is non-uniform at one or more edges thereof, for example, tapering, where movement of the joint may allow bone to slide past other bone without an intermediate implant section.

An aspect of some embodiments of the invention relates to a two section shoulder implant. In an exemplary embodiment of the invention, the implant is implanted in a shoulder so it both separates a Humerus from a Glenoid and between the Humerus and a tendon and/or in subacromial space. In an exemplary embodiment of the invention, this provides for treating multiple shoulder disorders, such as rotator cuff problems and osteoarthritis. In some embodiments, one section serves to help anchor or limit the motion of another section. In some embodiments, the use of multiple sections improves the stability of the shoulder joint.

Optionally, the two sections include a fluid communication channel so they can both be expanded and/or deflated via a single port. Optionally, the two sections have different wall thicknesses, for example, the subacromial section having a wall thickness of less than 50%, 20% or smaller percentages of the wall thickness of the Glenohumeral section.

In an exemplary embodiment of the invention, the two sections are connected by a bridge which is narrower than the two sections. Alternatively, one section is an extension that extends away from the other section.

In an exemplary embodiment of the invention, any of the implants used is seamless. Optionally or alternatively, the implant includes a port which self-seals when an inflation tube is retracted therefrom. Optionally or alternatively, the implant includes means, such as connecting sections, which limits a maximum thickness of the implant, for example, to less than 4 mm, less than 3 mm, less than 2 mm or intermediate thicknesses. Optionally, the implant has a final thickness of at least 1 mm, at least 2 mm or more. Optionally or alternatively, the implant includes one or more through passages between its two main faces, for example, to assist in controlling the shape of the implant during use and/or inflation.

In an exemplary embodiment of the invention, the implant comprises two walls with a cavity defined thereby in between with its total thickness set by the amount of inflation. Optionally, more than two layers are provided, for example, three, four or more layers. Optionally, some or all of the adjacent layers define isolated cavities therebetween. In some embodiments, two or more of the cavities do have fluid communication there between. Optionally different cavities have different liquids therebetween.

In an exemplary embodiment of the invention, the implant includes a mesh or other surface which is adapted to adhere to one part of the joint. Optionally or alternatively, the implant includes a surface which is adapted to not adhere to a part of the joint.

In an exemplary embodiment of the invention, the implant includes one or more anchors, for example, one or more anchors adapted to attach to bone and/or one or more anchors adapted to attach to cartilage.

In some embodiments of the invention, some or all of the implant is configured to allow a sliding motion between two surfaces thereof.

In an exemplary embodiment of the invention, the implant is pre-formed to have curved surfaces, for example, conforming to spherical surfaces expected in a joint.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Exemplary Shoulder Implant

Figure 2A:
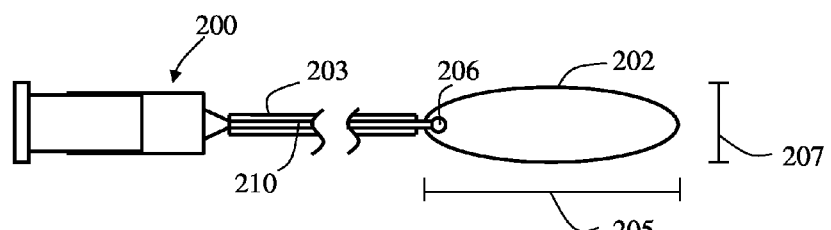
FIG. 2A is a cutaway schematic view of a portion of a prosthesis implantation and/or inflation device and an inflatable expandable prosthesis for the shoulder, in accordance with an exemplary embodiment of the invention.

Referring to FIG. 2A, a cutaway view of a portion of a prosthesis implantation and/or inflation device 200 and an expandable/inflatable prosthesis 202 is shown, in accordance with an exemplary embodiment of the invention. Similar or alternative designs of expandable prostheses and implantable balloons are described in PCT applications number PCT/IL2008/000347 and PCT/IL2005/000672, the disclosures of which are fully incorporated herein by reference. In an exemplary embodiment of the invention, however, the implant is specifically adapted for the glenohumeral joint, for example, by size, shape, consistency, strength and/or anchoring mechanism.

In an exemplary embodiment of the invention, inflatable expandable prosthesis 202 is circular or oval in shape when deflated, possibly delivered rolled or coiled, and when inflated resembles a cylindrical disc or ovoid. It should be understood, however, that many shapes may be chosen instead, in exemplary embodiments of the invention, for example, to match a particular shoulder geometry and/or dynamics. In some embodiments of the invention, prosthesis 202 is adapted to be inserted deflated into a patient's body through a cannula and/or covered by a flexible sheath 203. Optionally, the cannula is selected from cannulas of sizes of between 5 mm and 10 mm cannula. In an embodiment of the invention, a long axis 205 (x-axis) of inflatable expandable prosthesis 202 is approximately 1, 1.5 or 2 cm to 10 cm, optionally 3 cm to 6 cm in length when inflated. In some embodiments of the invention, the width 207 (y-axis) of inflatable expandable prosthesis 202 is approximately 0.5 mm to 20 mm when inflated. Optionally, inflatable expandable prosthesis 202 is 1.1, 1.5 or 2 mm to 9 mm in thickness. It should be understood that the deflated and/or inflated size of prosthesis 202 is adapted to fit for a patient's particular needs or to simulate the size and/or shape of the natural interior of a joint capsule, glenoid fossa and/or of a natural synovial membrane, in an embodiment of the invention, and therefore, prosthesis 202 does not necessarily conform to the size ranges given above.

In an exemplary embodiment of the invention, the implant is sized for the glenoid fossa and is provided, for example, in one of three sizes: 40×50, 50×60 and 60×70 (measurements in mm), with the shape being elliptical. For example, the ratio between the major and minor axes of the implant may be, for example, between 1:1.2 and 1:2.

In an exemplary embodiment of the invention, the size and/or thickness of the implant are selected according to a progression of the disease. For example, some diseases will narrow the glenohumal space so that a thinner implant may be desired. Other diseases may cause the creation of bone spikes which may or may not be removed during implantation. In such cases, a thicker implant may be used, to ensure a greater thickness than such spikes. Optionally, a plurality of implants are provided, each one with a thickening at a different part corresponding to a greater thickness for different parts of the Glenoid Fossa, according to the need at that part. Alternatively, for example, as shown below, the implant be selected to not cover all the fossa, but rather only needed parts thereof and/or parts of the labrum. Optionally, the implant is selected after and/or matched to a joint configuration after damaged cartilage and/or bone are removed. For example an implant of thickness (after inflation) of 0.5 to 6 mm may be chosen based on need. It is noted that the inflation/deflation can form a part of implant selection, with an implant chosen which can be fine-tuned by the inflation. Optionally, the implant includes two or more side by side chambers, optionally with separate inflation ports, whose separate inflation allows personalization of the implant thickness at different parts thereof.

In an exemplary embodiment of the invention, inflatable expandable prosthesis 202 is manufactured by dip molding and/or investment casting. In some embodiments of the invention, inflatable expandable prosthesis 202 is a seamless balloon-like structure made from biocompatible and/or biodegradable synthetic materials such as, but not limited to, PCL, PGA, PHB, plastarch material, PEEK, zein, PLA, PDO and PLGA, or any combination and/or family members thereof. Additionally, optionally and/or alternatively, inflatable expandable prosthesis 202 is manufactured from natural, biocompatible and/or biodegradable materials such as collagen and/or methyl cellulose. In some exemplary embodiments of the invention, the inflatable prosthesis 202 is manufactured from at least one non-biodegradable material such as polyethylene, polyurethane, silicon, and/or Kevlar®. In an embodiment of the invention, prosthesis 202 is comprised of a material which is about 100-200 microns in thickness, although, as with the other dimensions, the thickness dimension of the material is adapted depending on the intended use and/or the needs of the patient. In an exemplary embodiment of the invention, the thickness and/or material and/or a reinforcing feature (e.g., fibers) is selected to withstand the forces in the glenohumeral joint which may be, for example, 20 Kg, 50 Kg, 70 Kg, 100 Kg, 150 Kg, 200 Kg or intermediate or greater forces.

In some exemplary embodiments of the invention, inflatable expandable prosthesis 202 is adapted to elute pharmaceuticals such as anti-inflammatory drugs and/or antibiotics and/or pro-angiogenesis factors to promote healing. In some embodiments, inflatable expandable prosthesis is configured to release (for example by diffusion (e.g., through micropores in its wall) from an internal chamber and/or as external wall layers degrade and/or from pores in such walls) materials such as glucosamine and/or chrondroitin. Optionally or alternatively, the implant elutes an anti-adhesive and/or a slippery material.

In an exemplary embodiment of the invention, inflatable expandable prosthesis 202 is releasably attached to prosthesis implantation and/or inflation device 200. Optionally, prosthesis implantation and/or inflation device 200 (e.g., a manual syringe or pump) is adapted to inflate and/or deflate prosthesis 202 to a specific fill amount, which can determine an overall consistency, allow prosthesis 202 to be positioned in vivo. Optionally, device 200 is adapted to be separated (e.g., by retracting or by unscrewing, for example, with the device 200 detachable from port 206 by reverse screwing thereof) from prosthesis 202 after implantation, leaving prosthesis 202 at the implantation site. In some exemplary embodiments of the invention, prosthesis implantation and/or inflation device 200 includes a tube or catheter type structure 210 which interfaces with prosthesis 202 in the proximity of a sealing mechanism 206 which is located at the end of tube 210 nearest prosthesis 202. In an exemplary embodiment of the invention, mechanism 206 is a self-sealing port, for example, a duckbill valve or a ball valve. Optionally or alternatively, port 206 is simply a portion which elastically self seals when an inflation syringe is removed therefrom. Optionally or alternatively, other sealing methods, for example, such as known in the art, self-sealing or manual sealing, may be used.

In an exemplary embodiment of the invention, inflation is described for expansion. Optionally, other expanding mechanisms are used, for example, absorption of fluids from the surrounding wall or filing of the implant. Such an implant may be solid and not include a cavity. However, an advantage of an inflatable implant is that it can be deflated to reach a desired inflation amount.

Exemplary Placement and Consistency

Figure 2B:
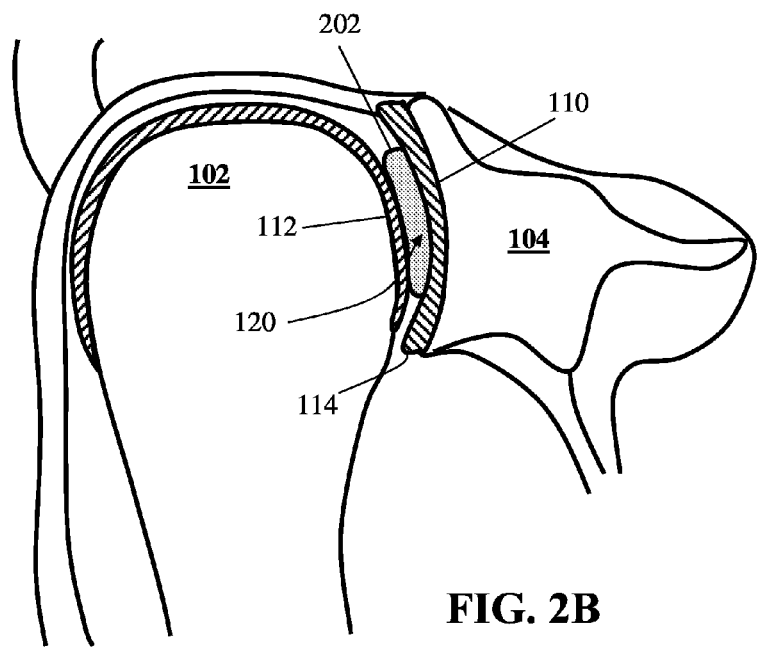
FIG. 2B is a cutaway view of an expandable prosthesis deployed in a glenohumeral joint, in accordance with an exemplary embodiment of the invention.

In an exemplary embodiment of the invention, inflatable expandable prosthesis 202 is introduced in the glenohumeral joint capsule between the humerus and glenoid cartilage surfaces to prevent injury thereof and/or to permit relatively unhindered or free shoulder movement. Optionally, alternatively and/or additionally, an expandable prosthesis comprises an inflatable structure and a sponge-like structure in combination. For example, one or both of the walls may include a sponge-like layer on the outside, or in a cavity defined by the implant walls. FIG. 2B is a cutaway view of inflatable expandable prosthesis 202 deployed in a glenohumeral joint capsule, in accordance with an exemplary embodiment of the invention. In some embodiments, a first surface of prosthesis 202 is at least occasionally and/or partially in contact with an external surface of a cartilage portion 112 of the humerus head/ball. Alternatively or additionally, a second surface of prosthesis 202 is at least occasionally and/or partially in contact with an external surface of a glenoid cartilage portion 110 and or with the labrum 114. In some embodiments, at least one of prosthesis 202 surfaces is smooth and allows gliding and/or frictionless motion of a cartilage portion in contact. Alternatively or additionally, at least one surface is coarse and/or comprising a frictional element (e.g., a mesh) thereby avoiding relative motion and/or encouraging adhesion with respect to a cartilage portion in contact. In an exemplary embodiment of the invention, placement and/or inflation and/or size of the implant are selected and/or modified according to a mechanical criterion, such as no contact between bones and/or a separation of, for example, 2, 3, 4 or smaller or larger or intermediate spacing in mm between the bones.

In an exemplary embodiment of the invention, the implant is chosen to have a wall thickness and/or inflation medium volume and/or ratio therebetween which provides a needed strength for example, resistance to forces of 100 Kg or more. In an exemplary embodiment of the invention, the implant is sized to fill the glenoid fossa 120, e.g., cover between 50% and 100% thereof, for example, between 70% and 90%. Optionally, the implant is selected and placed to abut against the labrum 114 at one or more locations, optionally being retained by the labrum 114. Optionally, the thickness is about 2-4 mm, for example, 2-3 mm, with wall of, for example, about 0.25 mm and a filling of saline.

In some embodiments, prosthesis 202 is configured to change its overall consistency to a specific chosen degree. "Consistency" will be considered herein as any property or combination of properties that directly relate to the prosthesis ability to maintain its shape under external stresses and/or retain it when these are removed, and for example, to the point of transfer from a rigid resistance to an elastic or plastic resistance under an applied force. Consistency may be the element density, softness, firmness, viscosity or any combination thereof. Prosthesis 202 consistency may be altered by the degree of relative inflation (vol. of actual inflation medium divided by vol. in maximal inflation) and/or by the properties (e.g., viscosity) of the inflation medium. In some embodiments, prosthesis 202 is deployed in a consistency that is similar, identical or equivalent to that of a synovial membrane or synovium, optionally the ones of the glenohumeral joint. It should be noted that a viscosity of normal synovial fluid is about 1 to 2 inch string (using a string test model: the max stretchable length of a measured fluid drop). Alternatively, the physician may choose another consistency according to need, which may or may not resemble a consistency of a cartilage or a bone. In an exemplary embodiment of the invention, prosthesis 202 has non-elastic wall.

In some embodiments, prosthesis 202 is fully inflated so it may be applied to firmly occupy a space, be uncompressible under unyielding forces and/or separate the two adjacent joint surfaces. In some embodiments, prosthesis 202 is not fully inflated at end of procedure so it is compressible under inward pressures. In some embodiments, the inflation device 200 and/or prosthesis 202 are configured and equipped to allow selective inflation/deflation and/or adjustments to a chosen volume and/or relative inflation. In some embodiments, prosthesis 202 is filled with Newtonian fluid (e.g., water or saline). Alternatively or additionally, the inflation medium includes a non-Newtonian fluid (e.g., hyaluronic acid) having a determined and/or variable viscosity. Alternatively or additionally, the inflation medium includes a lubricating material, either fluidic or non-fluidic, optionally a non-polar fluid such as lipid or oil. In some embodiments, only a minute quantity of material is introduced into prosthesis 202 inner volume, optionally inefficient to provide expansion, but still sufficient to reduce friction between the inner surfaces of the implant. In some embodiments, prosthesis 202 wall is sized and configured to have a chosen consistency when inflated partially and/or fully, optionally by combining specific wall thickness and wall material.

As will be noted below, inflation and/or placement and/or selection of the implant are optionally performed and/or modified to achieve certain desired functional and/or structural effects in a patient and are optionally personalized to that patient, for example, before or during and/or after implantation.

Exemplary Implantation Process

Figure 3D:
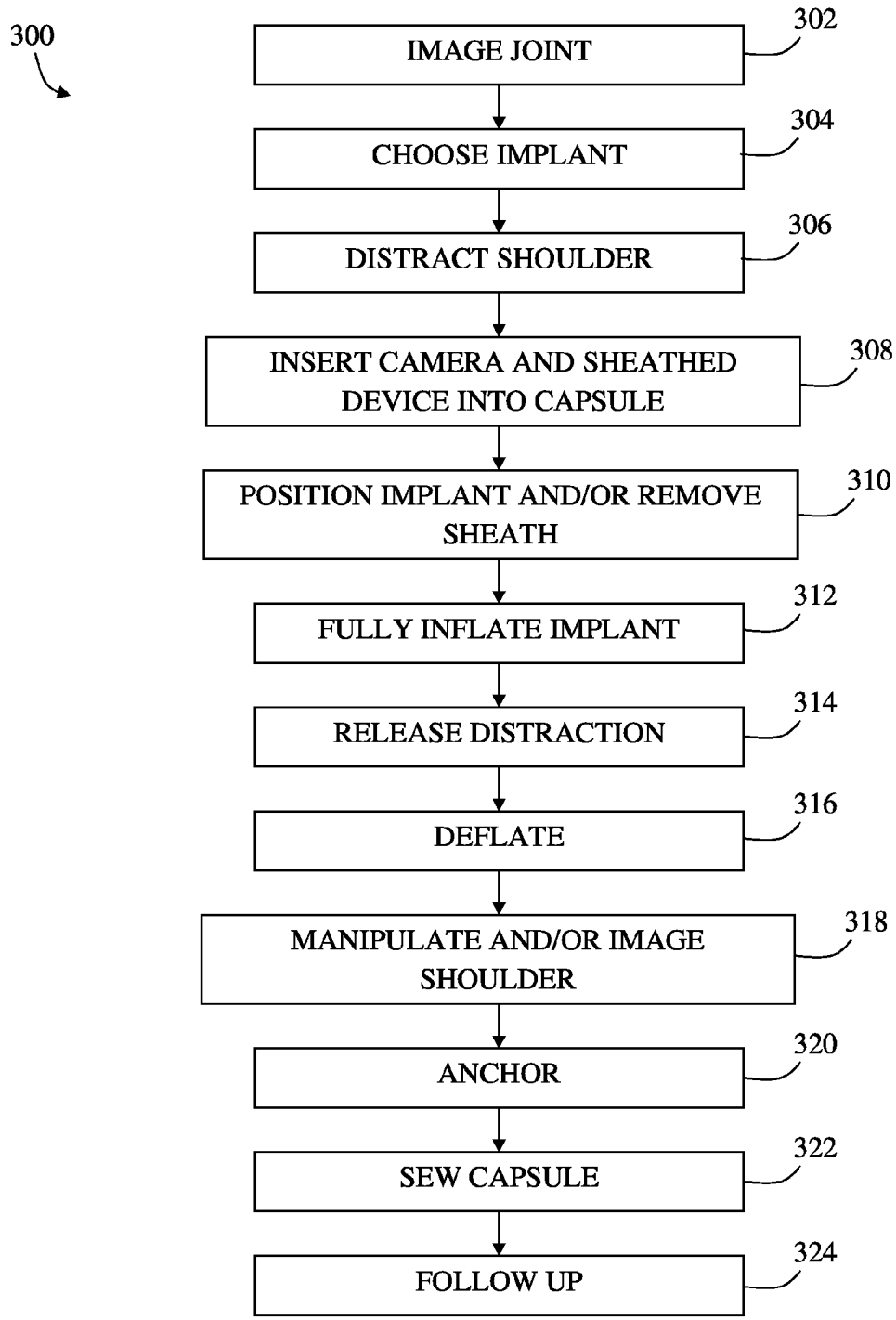
FIG. 3D is a flowchart of a method of implantation of a shoulder implant, in accordance with an exemplary embodiment of the invention.

Reference is now made to FIGS. 3A-C which illustrate different deployment stages of prosthesis 202, in accordance with an exemplary embodiment of the invention. FIG. 3D is a flowchart 300 of a method of implantation, in accordance with an exemplary embodiment of the invention.

At 302, the shoulder joint (e.g., including the glenohumeral joint) is optionally imaged. For example, MRI, CT, ultrasound, fluoroscopy and/or X-ray imaging may be used. Optionally or alternatively, invasive imaging using a camera on an arthroscope, may be used.

At 304, an implant (e.g., size, shape, inflation medium type, wall thickness and/or materials) is selected for the glenohumeral joint.

At 306, the shoulder is optionally distracted, for example, using methods known in the art.

At 308, a camera is optionally inserted into the joint, to image the procedure. Optionally or alternatively, the implant device is inserted, for example, using a separate cannula and/or covered by a flexible sheath 203. Optionally or alternatively, the device is uncovered when inserted into the capsule.

At 310, the implant is positioned, for example, adjacent the Glenoid Fossa 120. This can be seen, for example, in FIG. 3A, where a rolled up prosthesis 202, with two rolled up edges 204 is shown inserted into a glenohumeral joint. In other embodiments, the prosthesis is provided folded up in another manner or partly or completely expanded. Optionally, prosthesis 202 is maintained rolled up using a flexible sheath 203 and is allowed to—or caused to—unroll when the sheath is removed. In an exemplary embodiment of the invention, the implant is positioned, optionally under CCD imaging, ultrasound imaging or x-ray imaging, by manipulating delivery system 200 and/or an inflation and/or manipulation tube 210.

At 312, the implant is optionally inflated fully, optionally gradually, optionally to a fully deployed form and/or to another desired form. As shown in FIGS. 3B and 3C, progressive inflation causes the unrolling of wings 204, so prosthesis 202 is fully deployed. Optionally or alternatively, full inflation is used to provide distraction of the glenohumeral joint.

Optionally, once wings 204 are unfolded (or device otherwise unfolded), prosthesis 202 may not be re-folded for example when deflated. For example if portions of its wall irrecoverably (e.g., plastically) deform (e.g., including a metal insert therein) and/or if portions of its wall regain elastic properties once past a certain expansion.

At 314, the distraction is optionally released, partly and/or in full, for example, so that the functionality and/or positioning of prosthesis 202 can be assessed.

At 316, the implant is optionally deflated, for example, to reach a desired thickness and/or consistency, for example, a desired stiffness or a desired slippage behavior. Optionally or alternatively, the deflation is selected to maintain stability of the shoulder and/or of the implant. Optionally, act 314 is performed during or after 316.

At 318, the shoulder is optionally imaged and/or manipulated, for example to assess a functionality of the implant. In response to such imaging and/or manipulation, the implant may be repositioned, inflated and/or deflated, or possibly removed and/or a different material inserted therein. Acts 310-318 or any selective acts thereof may be repeated as needed, as part of a fine-tuning procedure whereby the implant characteristics are matched to the particular patient's need. The shoulder may also be distracted, as needed.

In an exemplary embodiment of the invention, a target of the fine tuning is prevention of contact between bones (or damaged cartilage) over a desired range of motion of the shoulder. Optionally or alternatively, a target of the fine tuning is ensuring a distance of, for example, between 2 and 4 mm between bone faces under a certain magnitude of an applied force or under no external stresses. Optionally or alternatively, a target of the fine tuning is that the shoulder move smoothly and/or that there is no dislocation. Optionally or alternatively, a target of the fine tuning is that the implant location is stable. Optionally or alternatively, a target of the fine tuning is to replace or modify functionality of a synovia between a humerus head and a glenoid fossa, at least for a period of time. The inflation tube and/or delivery system are optionally removed only after fine tuning is completed. In some embodiments, the tube is removed before final undistraction of the shoulder. Optionally, the inflation tube is thin and/or soft and/or flexible, to prevent damage thereby to the cartilage.

In an exemplary embodiment of the invention, the functional assessment is over a useful range of motion, which can include angular extents and/or arm positions. Optionally or alternatively, the motion is defined according to planned activities. Optionally or alternatively, reduction of pain by at least 50% or 70 (using a pain scale) is a target, for at least a certain range of angles. Optionally, restoration to a normal range of motion is provided. In an exemplary embodiment of the invention, a useful range of motion includes a range of angular motion that is at least 50% (in each direction) of a normal range. Optionally, the range is at least 70% of a normal range in each direction. Optionally or alternatively to estimating based on angular position, estimation is based on ability to move and/or not have pain, under conditions of loading of the joint by a weight, for example, 1 Kg, 5 Kg or 10 Kg or intermediate or greater forces.

Optionally, the desired function is a normal unhindered multiaxial motion of a human shoulder under loads of up to, for example, 10 Kg, 50 Kg or 100 Kg that is stabilized only by soft tissues.

In an exemplary embodiment of the invention, the tube removal causes and/or is accompanied by a sealing of port 206.

At 320, the implant is optionally anchored in place. While in some embodiments the implant naturally stays in place and in others, part of the implant adheres to tissue over time, optionally, anchoring is provided as part of the implantation procedure. Optionally, anchoring comprises providing a tissue adhesive between the implant and tissue. Optionally or alternatively, anchoring comprises sewing of a part of the implant, for example, an extension "ear" or "lip" thereof. Optionally or alternatively, anchoring comprises attaching a bone or cartilage anchor, for example screw-type, curved barb type, changing-cross-section type and/or linear bone anchor types. Some embodiments, for example, are self anchoring without a separate anchor or adhesive layer. Anchoring may also be performed earlier, for example, during or before any of 312, 316 or 316. For example, anchoring may be by pushing the implant against a surface so a barb thereon engages the surface.

At 322, the capsule is optionally sewed shut and the procedure completed.

At 324 follow up is optionally performed, for example, to asses implant functionality, for example, after a few days, weeks or months. Optionally, an additional implant is inserted if needed. Optionally or alternatively, an existing implant is removed and/or its level of inflation changed. Optionally, an implant is inflated by inserting a syringe into the joint and into the implant and inflating or deflating, as desired. Optionally, follow-up includes assessing the decomposition of a biodegradable implant.

Exemplary Implant and Anchoring Variations

FIGS. 4A-C and 5A-5E illustrate different prosthesis designs and anchoring configurations, in accordance with exemplary embodiments of the invention.

Figure 4A:
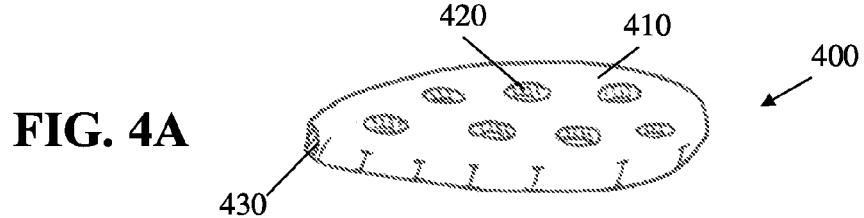
FIGS. 4A-C illustrate various prosthesis designs, in accordance with exemplary embodiments of the invention.

An exemplary prosthesis 400 is illustrated in FIG. 4A and includes a body 410 having an inflatable inner cavity sealed with a valve (optionally one-way valve) or plug 430. Optionally valve or plug 430 is to be deployed fixedly in-place (automatically or manually) in an inflation port after inflating prosthesis 400, for example by or after disconnecting an inflation device such as device 200. FIG. 4A illustrates an optionally feature of providing one or more connections 420 between opposite faces of the implant, optionally through openings. Through-hole(s) 420 provides a passage between two different, optionally opposing, surfaces of prosthesis 400, and optionally allows inward migration and/or buildup of fibrosis therein. Additionally or alternatively, the presence of at least one through-hole 420 stiffens an adjacent local portion of prosthesis 400 surface and/or limits its expansion to a predetermined size (e.g., in width or in height).

Figure 4B:
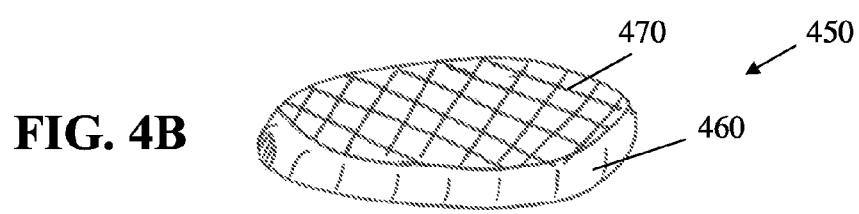

FIG. 4B illustrates a second exemplary prosthesis 450 which may have a body 460 similar in at least some characteristics to prostheses 202 or 400, while differing by at least having at least one surface covered with a mesh 470 or other adhesion encouraging or causing surface. In some embodiments, mesh 470 establishes at least one of: greater friction characteristics to the surface in-contact, anchoring to at least one joint surface, size or shape expansion limiting, improved fibrosis generation and/or fixation and/or changed overall prosthesis consistency.

Figure 4C:
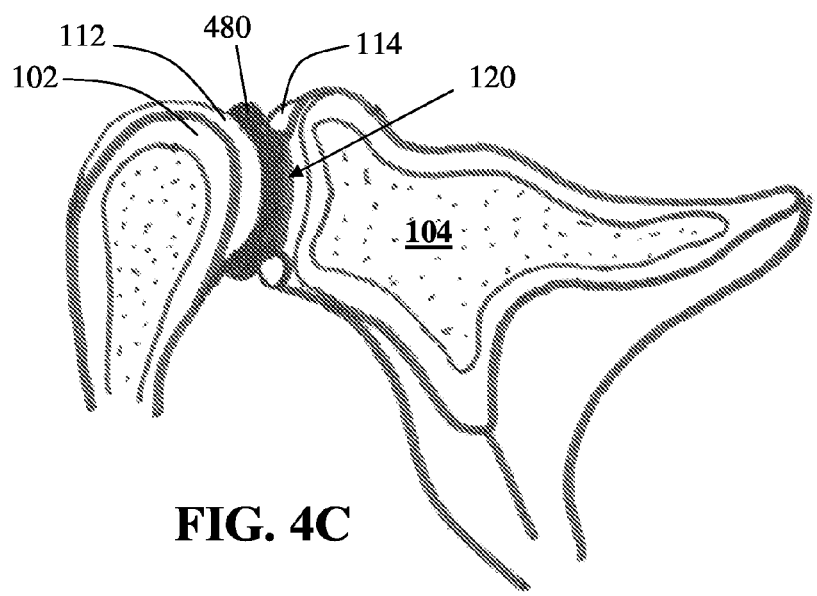

FIG. 4C illustrates a third exemplary prosthesis 480 deployed in position in a glenohumeral joint, according to an exemplary embodiments of the invention. In some embodiments, prosthesis 480 is sized and configured to enlarge the contact surface with the humerus ball, to establish a deepened "socket" than the one formed by the glenoid cavity and surrounding labrum and/or to cover the labrum. In some embodiments, prosthesis 480 is substantially flexible in at least one axis so it can take a general curvature between the humerus ball and glenoid socket. Alternatively or additionally, at least one wall portion or surface of prosthesis 480 is substantially pre-shaped. Optionally, the "socket" surface of prosthesis 480 (as suggested in FIG. 4C) is sized to fit inside the glenoid cavity and labrum, so it is substantially fixed in-place. Optionally or alternatively, one face of prosthesis 480 has a greater curvature than its opposite face. Optionally or alternatively, the portion of prosthesis 480 that lies over the labrum is thinner and/or is a non-inflating portion, than portions in the glenoid fossa.

Figure 5A:
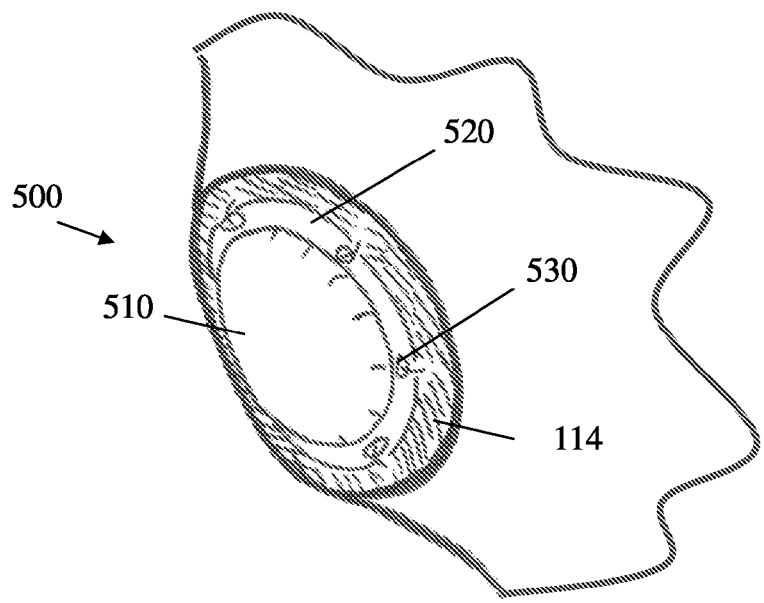
FIGS. 5A-5E illustrates various prosthesis shapes and anchoring methods, in accordance with exemplary embodiments of the invention.

Reference is now made to FIG. 5A showing yet another exemplary prosthesis 500 having a body 510 that may be similar to the above mentioned prostheses and/or an inflatable bladder or envelope. Optionally, prosthesis 500 further include a ring or a collar 520 that surrounds its circumference, which includes (e.g., pre-provided or added after insertion) at least one anchoring member 530, connecting it to the labrum 114. Similarly to prosthesis 480, prosthesis 500 is also optionally snuggly-fit into the glenoid cavity, whereby anchor (s) 530 facilitates a more substantial fixation in-position. Anchoring can be made by any anchors types known to art, including but not limited to surgical stitching, stapling, gluing, etc. Optionally or alternatively, rim/lip 520 may include a resilient member, such as a metal ring, to maintain its shape.

Figure 5B:
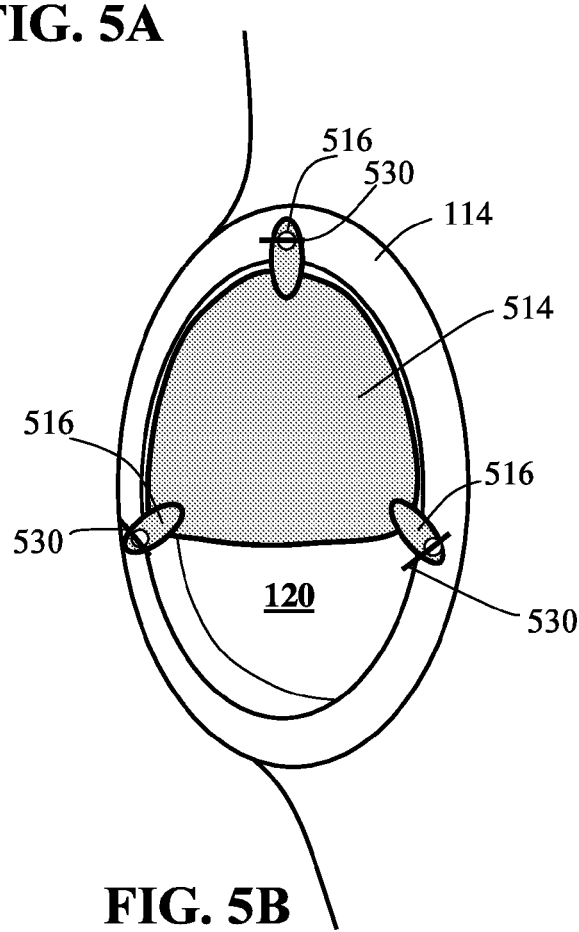

FIG. 5B shows an implant 514 which fills only part of glenoid fossa 120, for example, an upper or lower half. Optionally, the thickness of the implant is tapered towards the edge which meets the revealed fossa. This edge may be, for example, straight, concave, convex or wavy. Also shown is the use of three ears/extensions 516, each including an anchor 530 (e.g., a barb, a clip, a suture or a screw) for attachment to labrum 114. A smaller or greater number of ears may be used. Optionally, the implant includes more ears and some are removed prior to or during implantation, for example, to match angular locations along the labrum where such anchoring will be less problematic. In an exemplary embodiment of the invention, for example, 1, 2 or 4 anchors are used. The anchors may be uniformly or non-uniformly located along the labrum, depending, for example, on medical and/or mechanical considerations. Optionally, fewer than 7 or 6 anchors are used.

Figure 5C:
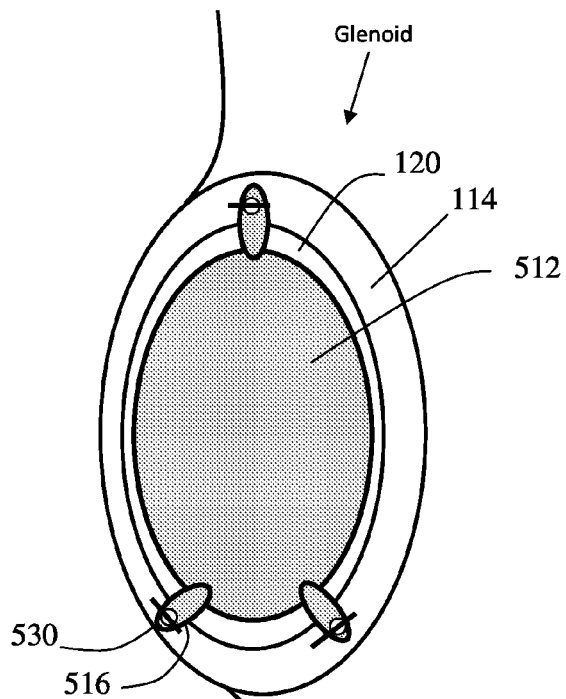

FIG. 5C shows an implant 512 which fills substantial all of glenoid fossa 120. Anchor may not be needed.

Figure 5D:
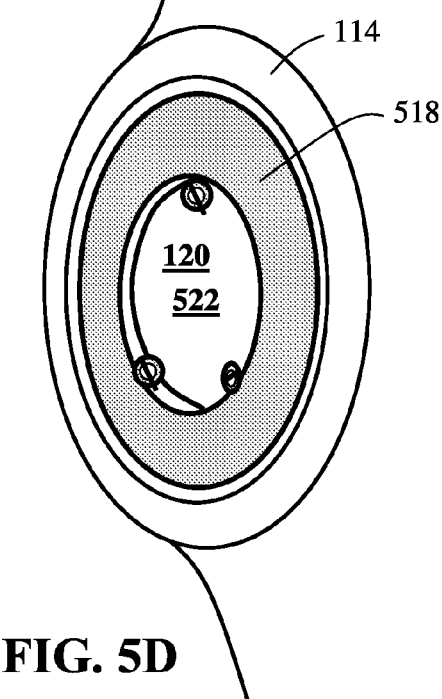

FIG. 5D shows an implant 518 in the shape of a ring with a central aperture 522. As shown, anchoring may be in the aperture, optionally using anchoring extensions (not shown). While the ring is shown to be ellipsoid, it may be round or have other shapes.

Figure 5E:
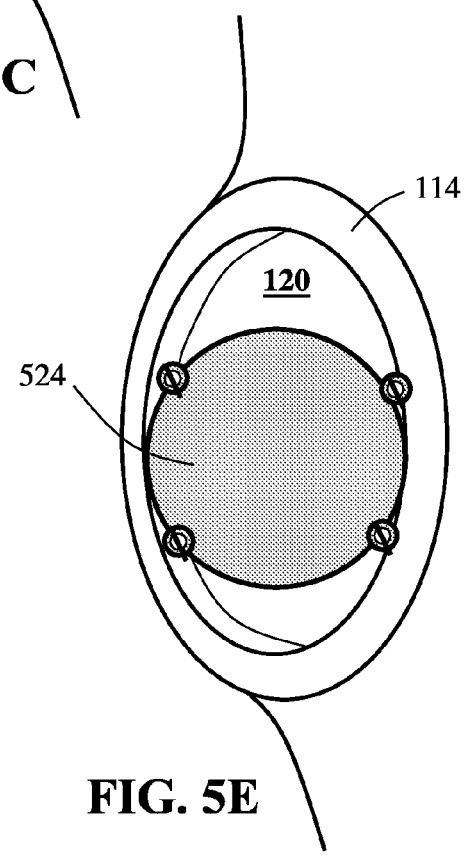

FIG. 5E shows an implant 524 which is circular or at least more circular than glenoid fossa 120. Optionally, the implant is held in place, at least in part by matching one of the radii of glenoid fossa 120. Alternatively, the implant may be smaller in radius than that radius. Optionally or alternatively, the implant may be ellipse-like with a main axis perpendicular to that of fossa 120.

In some embodiments, the port (e.g., 206) is positioned on the implant so it also lies within the fossa. In other embodiments, the port extends past the labrum 114 (e.g., like extensions 516. In some embodiments, the access and/or port is at an anterior superior or inferior portal to the joint and/or using the rotator interval portal.

Through Bone Delivery and Humeral Attachment

A glenohumeral implant may be inserted also in other ways, for example, via a channel formed in the humeral head. Optionally, such an implant is the same as described above, once deployed. Alternatively, such an implant is anchored to the humeral head, rather than the glenoid. Optionally, such an implant may be greater in surface area.

Figure 6A:
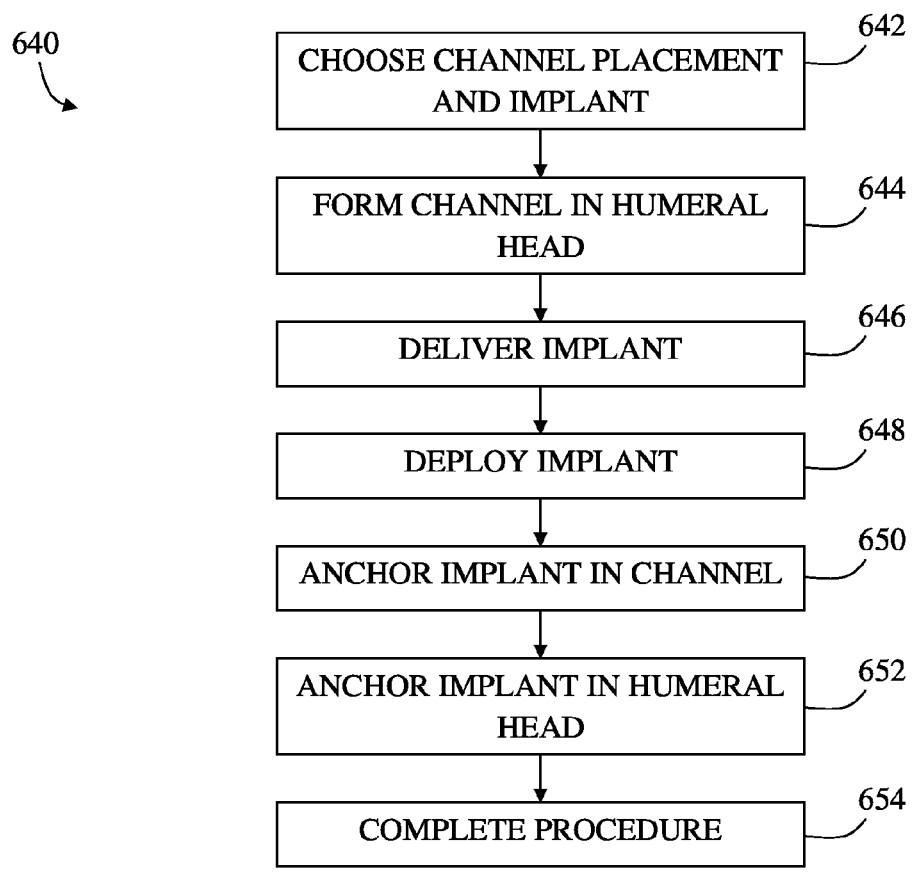
FIG. 6A is a flowchart of a method of implantation in a shoulder, including forming a channel in the bone, in accordance with an exemplary embodiment of the invention.
Figure 6B:
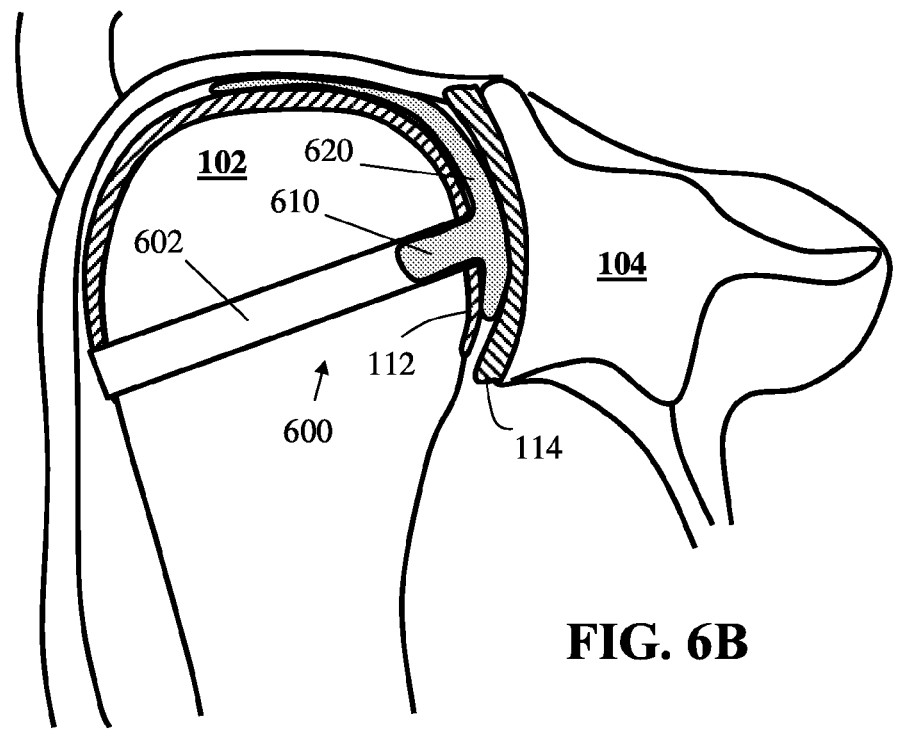
FIG. 6B is a cutaway view of an exemplary prosthesis delivered through a passage crossing the humerus head, in accordance with an exemplary embodiment of the invention.

FIG. 6B is a cutaway view of a prosthesis 600 delivered through a passage or channel 602 crossing the humerus ball, in accordance with an exemplary embodiment of the invention. FIG. 6A is a flowchart 640 of a method of implantation thereof, in accordance with an exemplary embodiment of the invention.

Prosthesis 600 (FIG. 6B) includes a body 620 and an optional anchoring portion 610 that protrudes into and is optionally coupled to the distal end of channel 602. The glenohumeral joint is optionally distracted.

At 642, A channel location and size and an implant are chosen, for example, according to considerations such as health of the humeral head, preexisting medical condition, and/or anatomical limitations.

At 644, channel 602 is formed in the humeral head. Optionally, channel 602 is drilled through the humerus head using known drilling means. Optionally, drilling is performed under imaging. Optionally, drilling is made according to a chosen path which is predetermined according to initial analysis and/or which is taken while drilling. Optionally, any debris formed during drilling is cleaned out of the joint, for example, by washing, suction and/or using a tweezers.

At 646, once channel 602 is formed, prosthesis 600 can be delivered in a collapsed form therein and expand, optionally self-expand and/or be inflated until reaching a chosen shape and/or size.

At 648, the implant is deployed, for example, by expansion. Optionally or alternatively, a tool or stylet is inserted into the implant and used to spread it out. Optionally or alternatively, the implant includes a rim ring (not shown) of a resilient material to spread it out and/or maintain its spreading. Fine tuning and adjustment may be carried out, for example, as described with respect to FIG. 3D.

At 650, implant 620 is optionally anchored in channel 602. Optionally, such anchoring is via an expanding protrusion 610 thereof. Optionally or alternatively, the protrusion is anchored using an anchor, for example as described above. In some embodiments, the implant is anchored or rests in the glenoid fossa and/or labrum, and slides freely with respect to the humeral head 102. Optionally, the implant is tethered to channel 602, for example, with a tight tether or with a tether which gives some freedom of motion. Optionally, the tether is attached to a part of the bone away from the surface of the humeral head. Optionally or alternatively, two implants are provided, one that is stable relative to humeral head and one that is stable relative to the glenoid fossa, which two implants slide over each other. In an exemplary embodiment of the invention, the inflation of implant 620 is via a port (not shown) in protrusion 610. Optionally, a plug used to seal the port also causes anchoring of protrusion 610, for example, by expansion thereof.

At 652 (which may be carried out before 650), the implant is anchored on the humeral head, for example, using an adhesive layer or barbs on the side of the implant that is near the humeral head (not shown). As shown in FIG. 6B, a significant portion of humeral head 102 may be covered by the implant, for example, over 50% of a surface area thereof. Implant 620 is optionally designed to taper at its edges. Also as shown, the location of protrusion 610 need not be symmetric with respect to implant 620.

At 654 the procedure may be completed (e.g., deployment means withdrawal, sewing, etc).

Two Section Implant

Many patients have more than one problem with the shoulder, which problem could be treated using an orthopaedic implant. Sometimes, osteoarthritis or other shoulder joint illnesses or trauma effects, affects several locations of the shoulder joint, for example, both the glenohumeral joint and the rotator cuff. A potential benefit of providing two therapies with one implant (besides reduction in cost and/or trauma) may also be the increased stability of the implant and/or shoulder. In an exemplary embodiment of the invention, a two section implant is used for treating, for example, rotator cuff injuries and glenohumeral joint problems.

Figure 7:
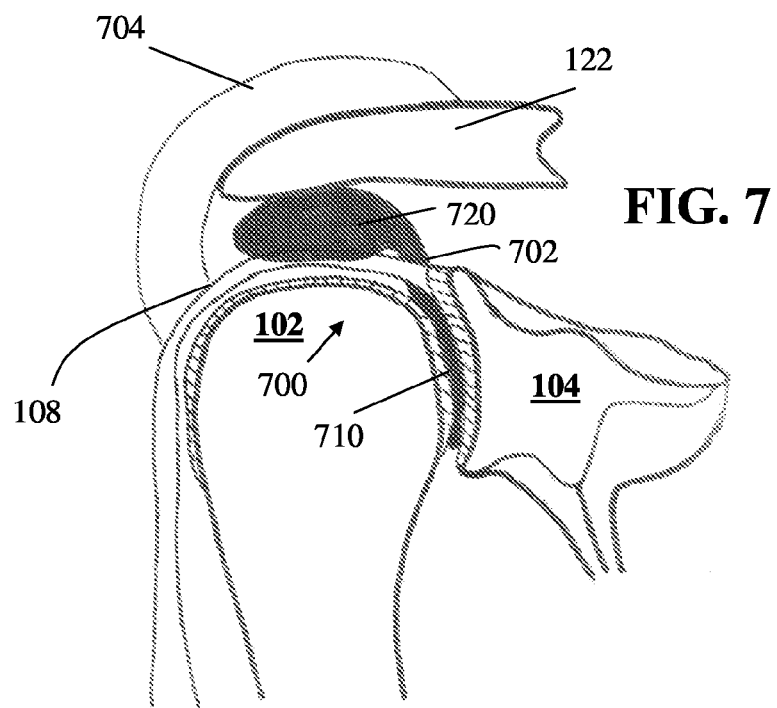
FIG. 7 is a cutaway view of an implantation of an exemplary prosthesis both a bursa simulating section and a glenohumeral section, in accordance with an exemplary embodiment of the invention.

Reference is now made to FIG. 7 showing a cutaway view of a prosthesis 700 which includes a synovium simulating portion 710 (or for otherwise treating a glenohumeral joint) and a bursa simulating portion 720 (or for otherwise protecting a tendon from contact with bone), located and allowing frictionless movement between a hard tissue and a soft tissue (such as between the acromion and the biceps tendon) and/or between two hard tissues (such as between the acromion and the humerus), in accordance with an exemplary embodiment of the invention. More details about the need and possible applications of a bursa simulating prostheses are described in international patent application number PCT/IL2008/000347, the disclosure of which is fully incorporated herein by reference. The mechanical properties of the two sections may be different, for example, being different wall thicknesses, different inflation properties, different biodegradability and/or permanency properties and/or different adherence properties. For example, one section may be inflatable and the other not or one section may be deflatable and the other not.

In an exemplary embodiment of the invention, one section has a pre-inflation thickness which is a factor of between 1 and 5 of the other section, for example, between 1.2 and 2. Optionally or alternatively, such factors are for an inflated implant.

In an exemplary embodiment of the invention, the two implant sections different in surface area by a factor of between 1 and 10, for example, between 2 and 5.

In an exemplary embodiment of the invention, the two implant sections different in thickness by a factor of between 1 and 10, for example, between 2 and 5.

In an exemplary embodiment of the invention, the two implant sections different in wall thickness by a factor of between 1 and 10, for example, between 2 and 5.

Section 720 may be provided for other uses as well. In one example, section 720 is provided in the subacromial space, for example, to increase shoulder stability, for example, by preventing uplift of the humeral head. In another example, section 720 is placed outside the glenohumeral joint capsule. In another example, section 720 is attached to a part of the humeral head. In another example, section 720 serves as a fluid reservoir for section 710, for example, providing medication and/or friction reducing fluid thereto, for example, for elution from section 710. Optionally or alternatively, section 720 is provided as a general drug eluting implant. Optionally or alternatively, section 720 serves as an anchor for section 710.

In an exemplary embodiment of the invention, section 720 is outside of the glenohumeral joint and generally outside of the capsule thereof, but optionally within the shoulder joint.

In an exemplary embodiment of the invention, section 720 has at least one smooth surface on which a tissue may continuously move in a non-hindered manner. Optionally or alternatively, section 720 acts as a shock absorbing and/or spring cushioning implant. Optionally or alternatively, section 720 acts as a filler occupying a subacromial space thereby restoring shoulder shape and/or avoiding inadvertent shoulder dislocation under normative motions.

FIG. 8A shows an example prosthesis 800 comprising a bursa section 802 and a glenoid section 804, connected by a bridge 810. In the example, shown, separate inflation ports 806 and 808 are provided for each section. Optionally, as noted above, one of the sections may be non-inflatable. Optionally, bridge 810 can serve to carry fluid. Optionally, bridge 810 includes a one way valve which prevents over-inflation of the bursa simulating portion by fluid from the glenohumeral section. The two sections may have a natural angle between them, or bridge 810 may be flexible enough to provide such an angle as needed. In an exemplary embodiment of the invention, bridge 810 is non-expandable and lies substantially flat where it crosses the labrum 114, for example, at a thickness of less than 1 mm or 0.5 mm. In an exemplary embodiment of the invention, the bridge (e.g., portion narrower and/or thinner than either sections and/or non-expandable section) has a length of between 2 and 30 mm.

FIG. 8B is a side view of an alternative two-section implant design 820 and FIG. 8C a top view of such a design. In this embodiment, bridge 830 is used for fluid flow and a single port 826 is provided in a bursa section 822 and also serves to inflate a glenohumaral section 824. As can be seen in FIG. 8C, the bridge may have a width, for example, selected to reduce sharp edges and/or improve the relative stability of location of the two sections.

Figure 9A:
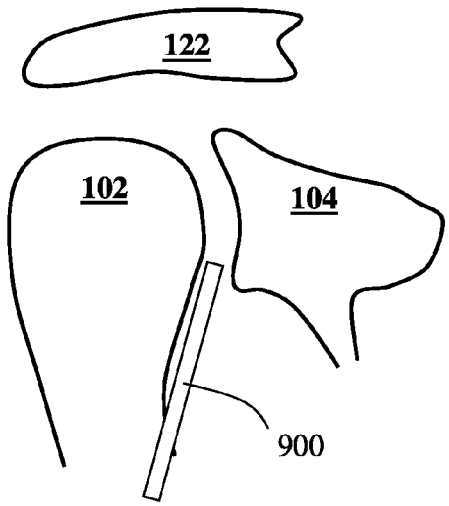
FIGS. 9A-9H illustrate various stages in a process of implanting a two section implant, in accordance with an exemplary embodiment of the invention.
Figure 9B:
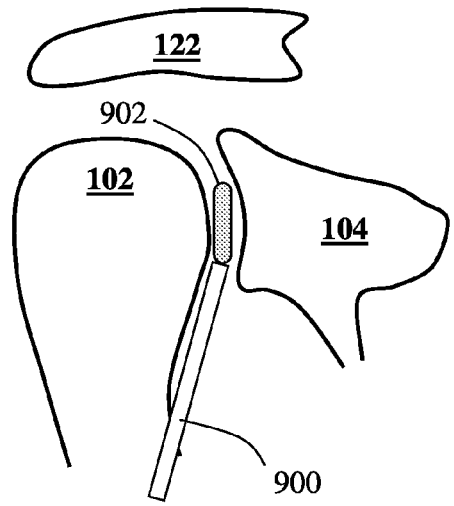
Figure 9C:
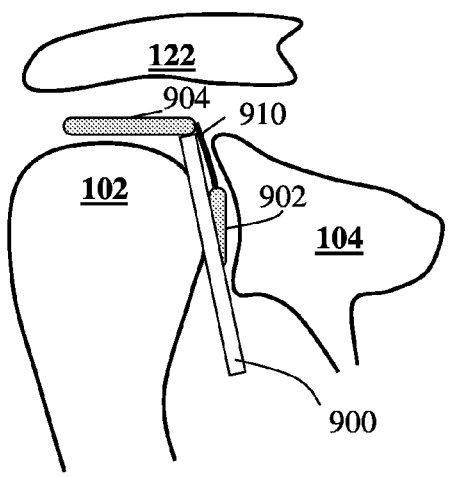
Figure 9D:
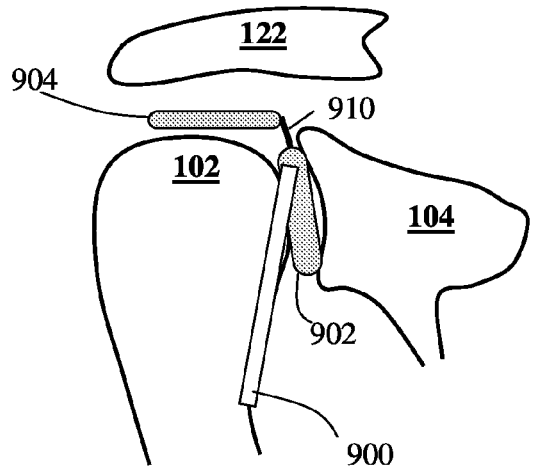
Figure 9E:
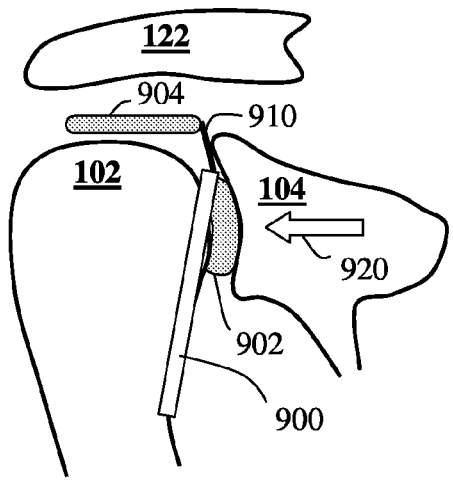
Figure 9F:
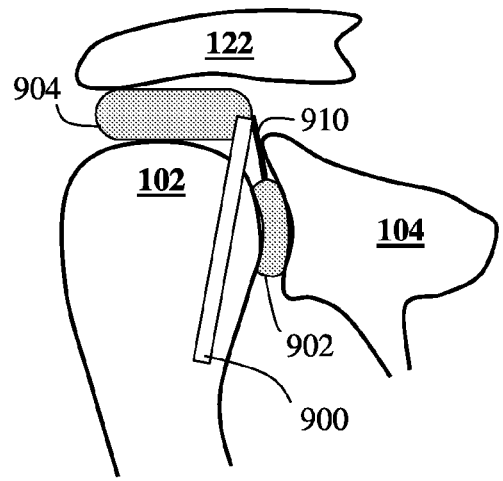
Figure 9G:
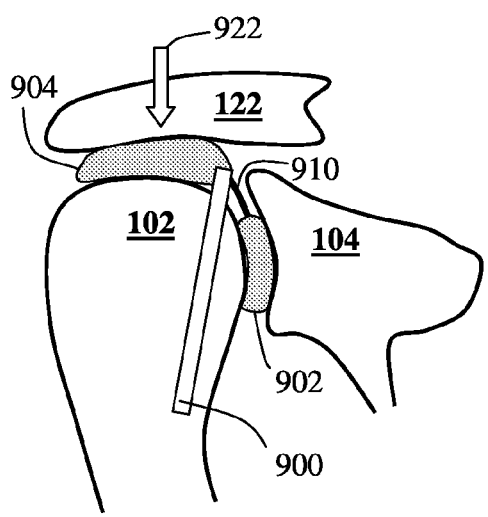
Figure 9H:
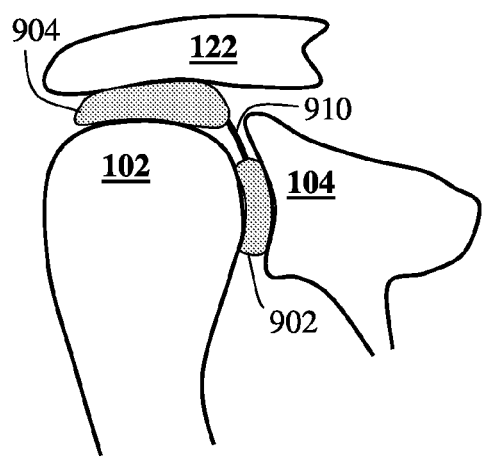
Figure 9I:
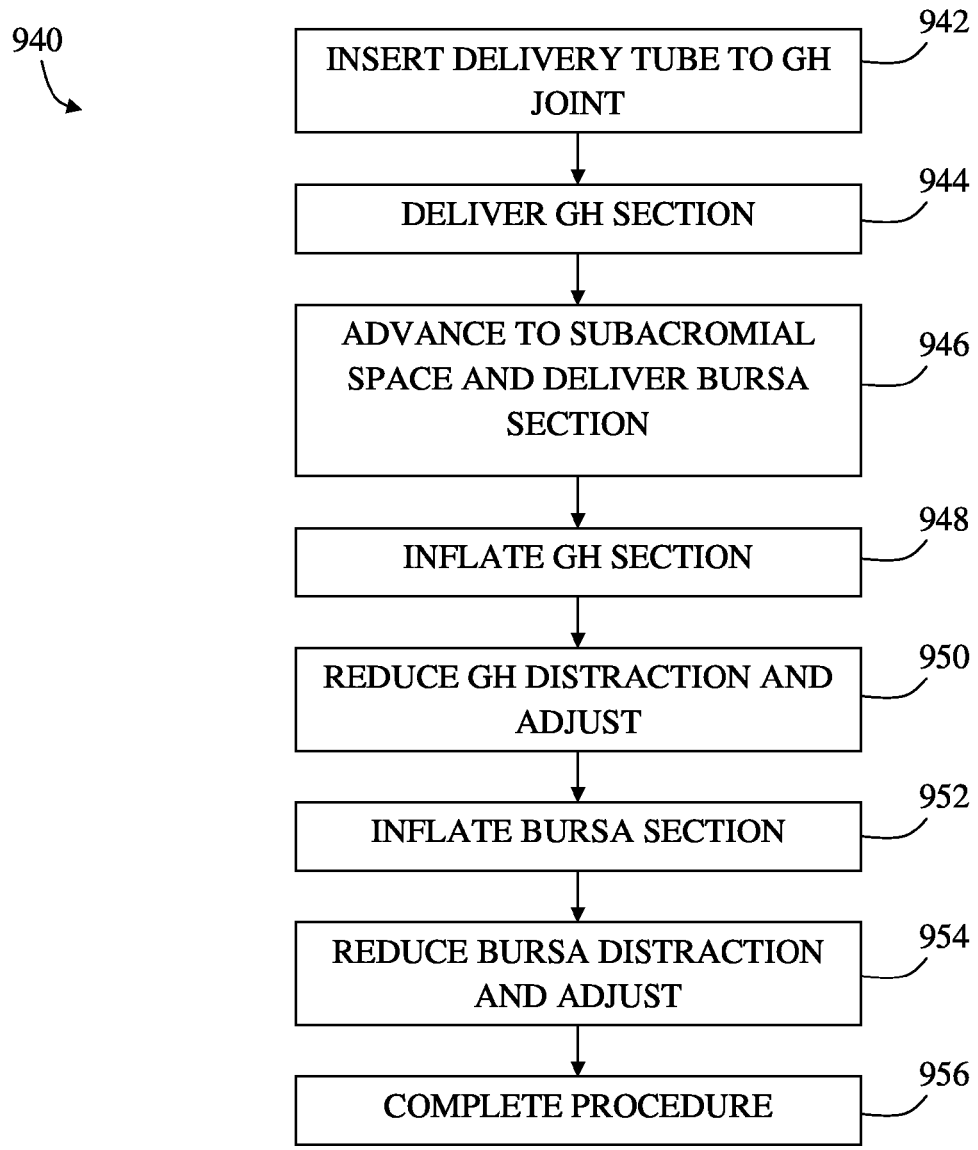
FIG. 9I is a flowchart of a method of implantation of a two section prosthesis, in accordance with an exemplary embodiment of the invention.

FIGS. 9A-9H illustrate an exemplary implantation method of a two section implant and FIG. 9I is a flowchart 940 of such a method, in accordance with an exemplary embodiment of the invention. In patients where the rotator cuff is torn it may be preferable to approach the bursa area also via the glenohumeral joint. In patients with no tear, it may be desirable to provide separate implants or to create a channel between the rotator cuff and the humeral head and/or through the rotator cuff. Alternatively, the bridge is provided to the side of the glenohumeral joint, rather than at its apex (near the rotator cuff).

At 942 (FIG. 9A), a delivery tube 900 is inserted into the glenohumeral joint.

At 944 (FIG. 9B), a glenohumeral section 902 is delivered into the joint, optionally rolled up and/or in a sheath.

At 946 (FIG. 9C) the delivery tube is advanced and/or retracted and a bursa section 904 is delivered to the subacromial space. In one example, the subacromial section is delivered to the capsule and then pushed into the subacromial section. Optionally, the glenohumal section is manipulated, for example, rotated, for this action, for example, so that the bridge points towards the subacromial space. In an alternative embodiment, first the bursa section 904 is delivered and then tube 900 is advanced and/or retracted and glenohumeral section 902 is delivered. In another embodiment, tube 900 is inserted to the capsule of the glenohumeral joint at a point between the joint and the subacromial space and then one section of the implant is delivered to one side of that point and one section to the other. Optionally, a curved or bendable delivery system is used to bypass muscles, ligaments, nerves, bones and/or vessel and/or articulate a tip of the delivery system.

Optionally, in case of a non-torn rotator-cuff, in which the glenohumeral capsule may be considered a separate space to the subacromial space, the introducer first enters the glenohumeral capsule and deploys section 902, is then pulled out and pushed over to surround the capsule and/or ligaments and/or bone and/or the joint itself (optionally, a curved introducer able to surround the capsule, for example, by 180 degrees, is used) and then enter the subacromial space. Optionally, the introducer travels inside the capsule, optionally bypassing the joint itself and a new opening is made in capsule to enter the subacromial space therefrom.

At 948 (FIG. 9D), section 902 is inflated, for example, to cause deployment thereof. Optionally, deployment is provided before act 946. Optionally, deflation and/or inflation is by attachment of an inflation tube to a port on section 902. Optionally, the sheath is removed from both sections prior to inflation of section 902. Alternatively, the sheath is only removed from sections which are being inflated.

At 950 (FIG. 9E) distraction of the glenohumeral joint is optionally reduced (e.g., in direction of arrow 920) and inflation is adjusted, for example, as described above with reference to FIG. 3D. Reduction in distraction and/or deflation may be performed after acts 952-954 and/or during such acts.

At 952 (FIG. 9F), bursa section 904 is expanded. Optionally, a separate inflation port is used. Alternatively, a valve in bridge 910 and/or a sheath on section 904 physically prevents inflation of bursa section 904 until glenohumeral section 902 is inflated. For example, such a valve may be a pressure sensitive valve (e.g., opens only above a certain pressure), or be a three-way valve. Alternatively, inflation is via a port on the bursa section, but a sheath prevents its expansion until after glenohumeral section 902 is deployed.

In an exemplary embodiment of the invention, the subacromial section of the implant is distally located in the delivery system. In others, the glenohumeral section is more distal. When deploying, a tubular expansion-prevention sheath may be provided over the section which is more proximal and is to be inflated later (or over both and then partially retracted). In embodiments where inflation of the proximal section is to be done first, the sheath may be replaced by a ring, mounted on an elongate element (e.g., flexible or rigid), with the ring mounted on and used to prevent expansion of only one section of the implant and the elongate section manipulated to remove the ring form that section when desired and/or to move it to another section. Optionally, the ring section is a flexible segment of a tube and a portion of the tube axially corresponding to the other implant section is apertures at its side so it does not interfere with expansion of that other implant section.

At 954 (FIG. 9G) the distraction of a subacromial space is optionally reduced (e.g., in direction of arrow 922) and the bursa section 904 adjusted, as needed.

At 956 (FIG. 9H) the procedure is completed, for example, by sealing the ports, removal of tools and/or sewing of the capsule and/or incisions.

FIGS. 10A-10D illustrate an alternative implantation approach, which may also be use for one section implants (e.g., by not delivering a bursa/subacromial section).

Figure 10A:
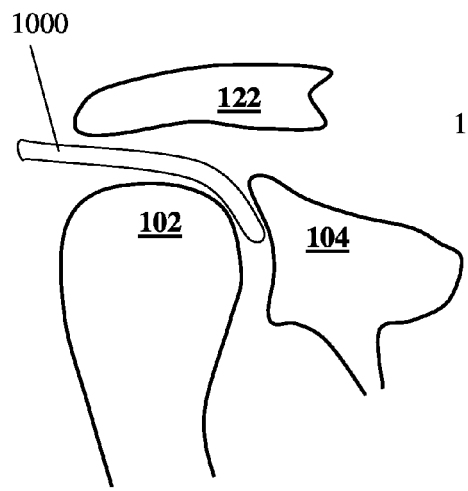
FIGS. 10A-10D illustrate various stages in a process of implanting a two section implant, in accordance with an alternative exemplary embodiment of the invention.

FIG. 10A shows inserting a delivery system 1000, for example a tube or a sheath through a subacromial space and into a glenohumeral joint. A curved or flexible delivery system may be used. In other embodiments (e.g., FIGS. 9A-9I) a rigid and/or straight system may be used.

Figure 10B:
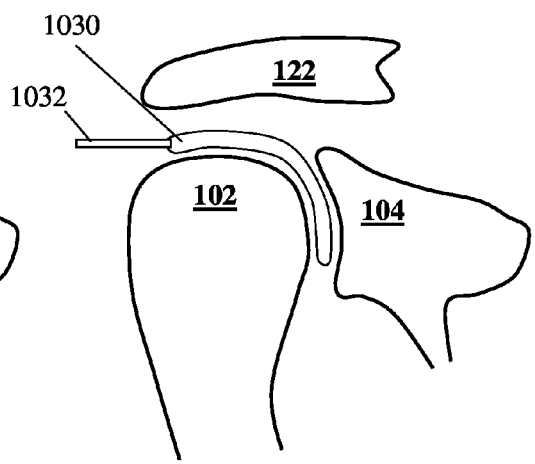

FIG. 10B shows the retraction of the delivery tube leaving an implant sheathed in a sheath 1030 and an inflation tube 1032 attached to a port thereon.

Figure 10C:
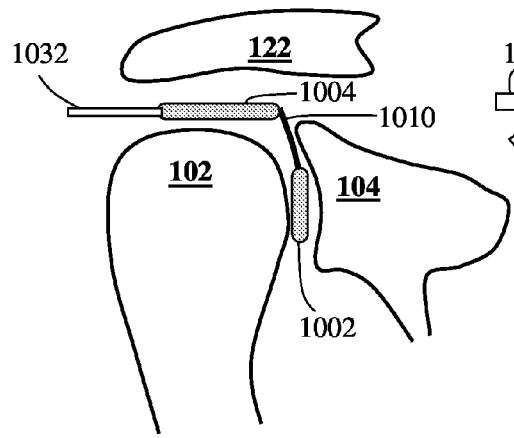

FIG. 10C shows the sheath removed, leaving a section 1002 in the glenohumeral space and a section 1004 in the subacromial space. Inflation, deflation and distraction may be as described above. Optionally, a valve is provided in bridge 1010, so that inflation of section 1004 above a certain pressure leaks into section 1002.

Figure 10D:
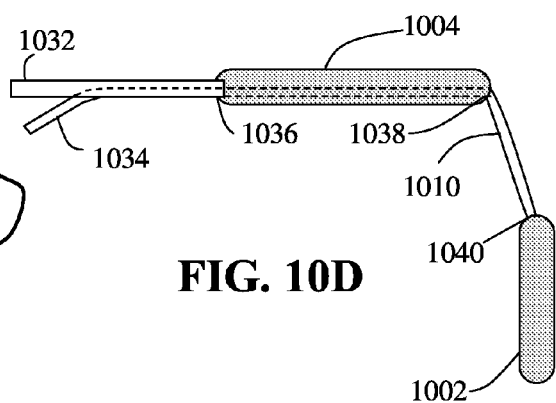

In an exemplary embodiment of the invention, shown in FIG. 10D, inflation tube 1032 encloses or is provided with an inflation tube 1034 which is dedicated for inflation of section 1002. Optionally, a valve is provided at point 1038 or at point 1040, or at any point in-between, to prevent leakage of pressure from section 1002 to section 1004 or from section 1004 to section 1002. Optionally, tube 1032 is attached at a valve/port 1036 and tube 1034 passes along or through tube 1032 to attach to a port 1038, 1040 or any port in-between, and/or directly to bridge 1010. The use of such separate inflation tubes can allow the independent inflation and/or deflation of the two sections 1002 and 1004. This type of separate inflation tubes may also be used with other embodiments described herein that include multiple cavities.

Optionally or alternatively, relative inflation of the two sections is controlled by providing height-limiters in one or both sections, which prevent over extension in a height direction of the inflated and limited section.

Kits

It should be appreciated that while the description has focused on methods and tools which may be used to carry out such methods, kits may be provided. One example of a kit is a set of one or more implants (e.g., of different sizes and/or shapes), instructions for use and a delivery cannula and/or sheath. Optionally, one or more anchors are provided. Another example of a kit includes in addition a bone drill. Another example of a kit includes multiple inflation tubes for multiple sections of an implant.

While the above has focused on implants for the glenohumeral joint, similar designs and/or methods may be used for other parts of the body (e.g., absent the particular adaptations to the glenohumeral joint, for example), such as an implant for other joints, an implant used only in a subacromial space, an implant separating two tissues from contact with each other, for example, ligament and bone, bone and bone soft tissue with soft tissue, or for space filling implants, such as to replace bones, bone section, soft tissue and/or generally urge one tissue against another or to prevent movement of a tissue. Such implants may be provided in accordance with some embodiments of the invention.

General

It is expected that during the life of a patent maturing from this application many relevant expansion technologies will be developed and the scope of the expansion is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for providing two therapies with one implant in a shoulder joint by affecting several locations of the shoulder joint, the method comprising:

providing a two section shoulder implant, said shoulder implant comprising a glenohumeral section sized and shaped for the glenohumeral joint, a bursa section sized and shaped for the subacromial space, and an elongated and non-expandable bridge connecting the glenohumeral section to the bursa section, and further comprising an inflation port;

inserting a delivery tube into the glenohumeral joint for delivering the glenohumeral section; followed by:

delivering deflated and rolled up the glenohumeral section into the glenohumeral joint using said delivery tube;

inflating and expanding the glenohumeral section, via said inflation port; followed by;

reducing distraction of the glenohumeral joint, and selectively adjusting inflation of the glenohumeral section;

pulling the delivery tube out of the glenohumeral joint;

inserting the delivery tube into the subacromial space for delivering the bursa section; followed by:

delivering deflated and rolled up the bursa section into the subacromial space using the delivery tube;

inflating and expanding the bursa section, via said inflation port; followed by;

reducing distraction of the subacromial space, and selectively adjusting inflation of the bursa section;

pulling the delivery tube out of the subacromial space; and sealing the inflation port.

2. The method of claim 1 wherein said inserting the delivery tube into the glenohumeral joint is followed by advancing and/or retracting the delivery tube prior to said inserting the delivery tube into the subacromial space.

3. The method of claim 1 comprising:

pushing the delivery tube over at least one of a glenohumeral capsule, ligaments, bone and the glenohumeral joint prior to said inserting the delivery tube into the subacromial space.

4. The method of claim 1 wherein the non-expandable bridge includes a pressure-sensitive valve.

5. The method of claim 1 comprising providing a tubular expansion-prevention device over one or both of the glenohumeral section and the bursa section.

* * * * *